United States Patent
Boyes et al.

(10) Patent No.: US 7,371,514 B2
(45) Date of Patent: *May 13, 2008

(54) SERIAL DERIVATIZATION OF PEPTIDES FOR DE NOVO SEQUENCING USING TANDEM MASS SPECTROMETRY

(75) Inventors: Barry E. Boyes, Wilmington, DE (US); Gordon R. Nicol, Middletown, DE (US); Hongbin Liu, Wilmington, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 10/892,870

(22) Filed: Jul. 16, 2004

(65) Prior Publication Data

US 2006/0014210 A1 Jan. 19, 2006

(51) Int. Cl.
*C12Q 1/00* (2006.01)
(52) U.S. Cl. ........................................................ 435/4
(58) Field of Classification Search ............... None
See application file for complete search history.

(56) References Cited

U.S. PATENT DOCUMENTS

| 5,821,063 | A | 10/1998 | Patterson et al. |
| 2003/0032056 | A1 | 2/2003 | Palmgren et al. |

FOREIGN PATENT DOCUMENTS

| WO | WO 00/43792 | 7/2000 |
| WO | WO 02/08767 | 1/2002 |
| WO | WO 02/095419 | 11/2002 |
| WO | WO 03/056299 | 7/2003 |

OTHER PUBLICATIONS

Kislinger et al. Curr Opin Mol Ther 2003, 5(3):285-293.*
Aebersold and Mann, 2003, Nature 422:198-207.
Aebersold and Goodlett, Chem. Rev. 101:269-295, 2001.
Cagney and Emili, Nat. Biotech. 20: 163-170, 2002.
Cardenas, et al., Rapid Comm. Mass Spectrum. 11:1271-1278, 1997.
Chen, et al., Journal of Computational Biology, 8(6), 571-583, 2001.
Claverol, et al., Mol. Cell. Proteomics 2: 483-493, 2003.
Cramer and Corless, Rapid Comm. in Mass Spectrom. 15: 2058-2066, 2001.
Dancik, et al., Journal of Computational Biology, 6, 327-342, 1999.
Eng, et al., J. Am. Soc. Spectrom., 5:976-989, 1994.
Ficarro, Scott B. et al., Phosphoproteome Analysis by Mass Spectrometry and its Application to *Saccharomyces cerevisiae*, Nature Biotechnology, 2002; 19:301-305.
Goodlett, David R. et al., Differential Stable Isotope Labeling of Peptides for Quantitation and de novo Sequence Derivation, Rapid Commun. Mass Spectrom, 2001; 15:1214-1221.
Gu et al., J. Am. Soc. Mass Spectrom. 14: 1-7, 2003.
Hunt, et al., PNAS 83: 6233, 1986.
Keough, T. et al., A Method for High-Sensitivity Peptide Sequencing Using Postsource Decay Matrix-Assisted Laser Desorption Ionization, Proc. Natl. Acad. Sci., 96:7131-7136, Jun. 1999.
Keough, T. et al., "Atmospheric Pressure Matrix-Assisted Laser Desorption/Ionization Ion Trap Mass Spectrometry of Sulfonic Acid Derivatized Tryptic Peptides," Rapid Commun. Mass Spectrom 2001, 15: 2227-2239.
MacCoss et al., PNAS 99: 7900-7905, 2002.
Mann, et al., 2001, Ann. Rev. Biochemistry 70:437-473.
Mann and Jensen, Nat. Biotech. 21: 255-261, 2003.
Mann & Wilm, Anal. Chem., 66:4390-4399, 1994.
Munchbach et al., Anal. Chem. 72: 4047-4057, 2000.
Person, et al. Chem. Res. Toxicol 16: 598-608, 2003.
Sze, Siu Kwan et al., "Top-Down Mass Spectrometry of a 29-kDa Protein for Characterization of any posttranslational modification to within one residue" PNAS 99: 1774-1779, 2002.
Taylor and Johnson, Rapid Communications in Mass Spectrometry, 11, 1067-1075, 1997.
Uttenweiler-Joseph et al., Proteomics 1: 668-682, 2001.
Zabrouskov et al., Mol. Cell. Proteomics 2:1253-1260, 2003.
Bonetto, Valentina et al., "C-Terminal Sequence Analysis of Peptides and Proteins Using Carboxypeptidases and Mass Spectrometry after Derivatization of Lys and Cys Residues", Analytical Chemistry, vol. 69, No. 7, 1997, pp. 1315-1319.
Peters, Eric C. et al., "A Novel Multifunctional Labeling Reagent for Enhanced Protein Characterization with Mass Spectrometry", Rapid Communications in Mass Spectrometry, vol. 15, No. 21, 2001, pp. 2387-2392.
Liu, Hongji et al., "Homogeneous Fluorescent Derivatization of Large Proteins", Journal of Chromatography A, vol. 927, No. 1-2, 2001, pp. 77-89.
Kuroda, N. et al., "Solution-Phase Automated Synthesis of Tripeptide Derivatives", Chem. Pharm. Bull., vol. 49, No. 9, pp. 1138-1146, 2001.
Tomlinson, Andy J. et al., "A Strategy for Sequencing Peptides from Dilute Mixtures at the Low Femtomole Level Using Membrane Preconcentration-Capillary Electro-Phoresis-Tandem Mass Spectrometry (mPC-CE-MS/MS)", J. Liquid Chromatography, vol. 18, No. 18-19, pp. 3591-3615, 1995.
Falick, A.M. et al., "Derivation of Hydrophilic Peptides for Liquid Secondary Ion Mass Spectrometry at the Picomole Level", Analytical Biochemistry, vol. 182, No. 1, pp. 165-169.
Communication from EPO dated Feb. 8, 2006, enclosing EP Search Report for EP Application No. EP 05013477, counterpart to U.S. Appl. No. 10/892,870.

* cited by examiner

*Primary Examiner*—Ralph Gitomer
*Assistant Examiner*—Bin Shen

(57) ABSTRACT

Serial derivatization by chemical reactions of analytes for mass spectrometry is disclosed. The derivatizations enhance the use of MS techniques for analyzing protein samples, particularly when the sequence of a polypeptide is determined by tandem MS/MS. Accurate mass analysis techniques are described for use in sequencing polypeptides, together with the use of sequencing data in protein analysis.

11 Claims, 9 Drawing Sheets

SERIAL DERIVATIZATION OF PEPTIDES FOR DE NOVO SEQUENCING USING TANDEM MASS SPECTROMETRY

BACKGROUND

Proteins are the fundamental biological units of cell structure and are formed from linear sequences of amino acids linked together by peptide bonds. This primary amino acid sequence determines the three dimensional characteristics and the function of the protein. There are twenty common amino acids, each with an amino group, a carbon atom with a unique side chain, and a carboxyl group. During mRNA translation on ribosomes, the peptide bond backbone of a protein is sequentially formed by bonds linking the terminal carboxyl group of one amino acid to the N-terminal amino group of the subsequent amino acid. The resulting linear chain of various amino acids has a first amino acid, the N-terminal amino acid with an amino group, and a final amino acid, the C-terminal amino acid, with a carboxyl group. Although proteins vary in length from a few peptides for peptide hormones to over 1500 amino acids, most proteins are generally about 100 to 300 amino acids long.

Because the structure of proteins is directly related to ultimate physiological function, determining the amino acid sequence of proteins has long been a basic endeavor in biomedical research and medicine. Traditionally, amino acid analysis involved determining a relative percentage of each amino acid present in a digestion of a purified protein and determining of the identity of individual peptide residues using laboratory chemistry. Protein sequencing was a laborious effort involving enzymatic digestions of a large amount of a purified protein into peptide fragments, followed by Edman degradations and alignment of overlapping sequences. Currently, reflecting the growing need for more accurate methods of protein sequencing, tremendous advances have been made in protein sequencing using mass spectrometry (MS). DNA genome sequencing, computer informatics, and sensitive protein analysis methodologies using MS are interfacing with classical protein chemistry to greatly advance the emerging field of scientific research known as proteomics.

Proteomics is the field of protein research that studies the large scale or global analysis of the protein complement of an organism (Aebersold and Mann, 2003, Nature 422:198). Proteomics is uniquely important in research, diagnostic, and clinical applications because it relates information from various technical disciplines, including chemistry, genetics, cell imaging, and chip- or microarray-based protein or DNA analyses, to cell function and physiology. In practice, proteomics requires detailed analyses of complex data for a large number of proteins in a short time period. Parameters of protein analysis include not only primary amino acid sequence, but also deletions, splice rearrangements, polymorphisms, mutations, substitutions, and other post-translational modifications (PTMs), such as phosphorylation, acetylation, nitration, sulfonation, oxidation, methylation, glycosylation, cross-linking. High throughput analysis of proteins and their related forms is critical for research in biology, physiology, and medicine and can be used in clinical diagnostic applications.

Mass spectrometry (MS) is a potentially valuable tool in proteomics because highly sensitive measurements of mass can identify some proteins by their amino acid sequence. (Aebersold and Goodlett, Chem. Rev. 101: 269-295, 2001; reviewed in Mann, et al., 2001, Ann. Rev. Biochemistry 70:437; Kinter and Sherman, Protein sequencing and Identification Using Tandem Mass Spectrometry, Wiley, N.Y., 2000). Because each amino acid or chain of amino acid residues can theoretically be detected by an accurate measurement of its mass, a sufficiently accurate measurement of mass allows the identification of the individual amino acids. When the sample processing and MS techniques are highly accurate, the actual sequence of amino acids that form a polypeptide molecule can be determined. Further, if a highly accurate and reliable method detects a deviation from the known mass for an amino acid, this can indicate that the amino acid has been modified, thus allowing detection of the modifications to protein structure described above that are often highly important in proteomics research, such as deletions, splice rearrangements, polymorphisms, mutations, substitutions, and post-translational modifications.

Mass spectrometry (MS) involves the analysis of ionized analytes in a gas phase using an ion source that ionizes the analyte, a mass analyzer that measures the mass-to-charge (M/Z) ratio of the ionized analytes, and a detector that registers the number of ions at each m/z value. The MS apparatus may also be coupled to separation techniques to improve the ability to analyze complex mixtures. Further, MS instrument combinations can be made to enhance sensitivity and selectivity. A wide range of MS instruments are available for use in protein sequencing. Regarding ion source, electrospray ionization (ESI) and matrix-assisted laser desorption/ionization (MALDI) are two commonly used techniques to ionize the proteins or peptides for analysis. ESI ionizes the analytes from a solution and MALDI desorbs and ionizes the sample, using a "matrix" that encourages desorption and ionization when exposed to light energy. MALDI produces predominantly singly charged ions from peptides. As described in more detail below, tandem MS/MS is a technique that uses at least two MS components and is a commonly used methodology for MS analysis of polypeptides.

There are several types of mass analysers, including ion trap, time-of-flight (TOF), quadrupole, magnetic sector, and Fourier transform ion cyclotron (FT-MS) analyzsers, each varying in analysis characteristics. These analysers may be run separately or assembled in tandem to maximize sensitivity and strengths of MS analysis. For example, a MALDI ion source is usually coupled to a TOF analyser, but may also be coupled to quadrupole ion-trap and to combined TOF instruments or FT-MS. For example, in TOF-TOF, two TOF sections are separated by a collision cell. In the hybrid quadrupole TOF apparatus, the collision cell is placed between a quadrupole mass filter and a TOF analyser. These examples illustrate how "tandem" mass spectrometry apparatus may be assembled from intact MS apparatus or selected components of the instruments. The fundamental characteristic of tandem MS is the structural information obtained from the fragmentation pattern of the ion. The design of the tandem MS/MS instrument allows versatility and increased sensitivity depending on the goal of the analysis and the chemical composition of the analyte. Of the MS equipment available, MALDI-MS/MS is a preferred method for peptide analysis, although others may be used. Aebersold and Goodlett, 2001; Cramer and Corless, Rapid Comm. in Mass Spectrom. 15: 2058-2066, 2001; see Aebersold and Mann, 2003 for other MS instrument combinations.

Polypeptide analysis by mass spectrometry is facilitated by the ability to obtain an accurate mass measurement of a group of peptides derived from a protein by fragmentation that occurs at specific amino acid sequences after using specific cleavage enzymes for proteolysis. The principle behind protein identification assumes that proteins of different amino acid sequence will, after proteolysis with a defined protease, produce a collection of peptides the masses of which constitute protein mass fingerprints unique to a specific protein. If a sequence database containing the specific protein sequence is searched using selected masses based on the experimentally and accurately observed peptide mass fingerprint, combined with the fragmentation rules of the protease, then the protein is expected to be correctly identified within the database. As described in more detail below, there are several circumstances where the experimentally observed mass spectra do not translate into a correct prediction of the actual protein composition or sequence.

Protein identification by this method involves a few basic steps: (i) Peptides are generated by digestion of the sample protein using amino acid sequence-specific cleavage reagents that allow the residues at the carboxyl- or amino-terminus to be known with a reasonable degree of certainty. For example, the enzyme trypsin leaves arginine (R) or lysine (K) at the carboxyl-terminus of digestion fragments. Accordingly, the N-termini of tryptic peptides (except for the N-terminal one) may be identified as the amino acid following a K or R residue in the protein sequence. (ii) Following digestion, the masses of peptides or polypeptides are measured as accurately as possible in a mass spectrometer. (iii) The experimental protein fragment mass data are run through a computer and compared with data in a computer database and using the rules that apply to the proteolytic method used in the experiment to generate a list of theoretical masses that are compared to the set of measured masses. (iv) An algorithm is used to compare the set of measured peptide masses against those sets of masses predicted for each protein in the database and to assign a score to each match that ranks the quality of the matches. This approach is frequently called "in silico" digestion and the correct protein identification by mass analysis depends on the correlation of the measured masses with corresponding data contained in a database. However, several difficulties exist with this approach. Obviously, for a protein to be identified its sequence has to exist in the sequence database being used for comparison. Also, digests of protein mixtures present a problem for mass analysis because it is not readily apparent which peptides in the complex peptide mixture originate from a specific protein. An increase in accuracy of measurement will decrease the potential error for matching an experimental mass to a corresponding mass in a sequence database, and therefore will increase the stringency of the database search.

If a pure protein is digested, and the resulting peptide masses are compared with the list of peptide masses predicted for that protein, two observations are typically made. First, not all of the predicted peptides are detected. Second, some of the measured peptide masses are not present in the list of masses predicted from the protein. The first problem, the missing masses, is usually due to a number of problems that can occur both before and during mass spectrometric analysis such as poor solubility, selective absorption, ion suppression, selective ionization, very short or very long peptide length, missed or inappropriate proteolytic cleavage or other artifacts that cause sample loss or make specific peptides poorly detected or undetectable by MS. This is a critical drawback because missing peptide masses may contain meaningful biological information. Unfortunately, it is not possible to distinguish between trivial and meaningful missing masses without further experimentation. Therefore, unassigned peptide masses are a significant problem for protein identification by mass analysis and probably the single biggest source of misidentifications or missed identifications.

Fragment ion spectra are generated by a process called collision-induced dissociation (CID) in which the amide bonds of a peptide are broken, followed by recording of the fragment ion spectrum. Cleavage of amide bonds results in b-ions (containing the N-terminal) and y-ions (containing the C-terminal). High quality MS/MS spectra of tryptic peptides typically show prominent b and y-ion series. If only these two ions were produced for every amide bond in a 10 residue peptide, the fragment ion spectrum would contain 18 peaks. Ideally, long stable ion series of predominately either the b or y-type would be recovered. In reality, peptide fragmentation is variable and moiety dependent, which leads to gaps and difficulties in analysis. Determining the identity and sequence of a peptide from its MS/MS spectrum is complicated both by the variety and variability of the fragment ions produced. Factors that complicate interpretation of MS/MS spectra are missing ion subsets, internal rearrangements, subsequent fragmentations, and multiple charge states. Also to be considered are the relationship of fragment ion peak intensity to ion series origin and fragment masses, influence of amino acid residues and their derivatives, on neighboring amide bond cleavages, and the link between amino acid composition and neutral loss fragmentation.

There are currently several approaches to MS protein de novo sequencing that vary with the size and purity of the protein to be analyzed. Although some data have been published, the MS sequencing analysis of partially purified undigested proteins (termed top-down sequencing), or expression analysis of proteins from whole cells, is still technically difficult partly because of the sample complexity (Zabrouskov et al., Mol. Cell. Proteomics 2:1253, 2003; Sze et al., PNAS 99: 1774-1779, 2002).

Tandem MS analysis of peptides followed by computerized database searching is also common in high-throughput proteomics research. Recent advancements in multidimensional separation technologies and automated data collection and analysis have further increased the throughput of this method for analyzing polypeptides in biological samples. However, a major drawback of this method remains a strict dependence on high quality experimental MS spectra because a theoretical peptide sequence is determined by matching the experimental spectra with the theoretical ones generated in silico. Although more and more genomes of different organisms are being sequenced, the databases still fall short of the entire collection of model organisms currently employed in biological research today. In addition, genome-derived predicted polypeptide sequence information often fails to reliably predict actual polypeptide information due to database errors, imperfect knowledge of transcript splicing (often employed in eukaryotic cells) as well as post-transitional modifications of polypeptides. The number of post-translational chemical and enzymatic modifications known to occur for proteins and peptides continues to increase. Currently, over 200 post-translational modifications of proteins are known. As the variety, breadth and frequency of such modifications are appreciated, the probability of perfect mass spectral matches to database-generated MS spectra must decrease. Thus, these biological processes may greatly hamper database searching and accurate sequence determination of proteins in biological samples.

Recent publications show that improved approaches of MS analysis can identify protein isoforms originating from alternative mRNA splicing, single-point mutations, and co- and post-translational modifications (reviewed by Mann and Jensen, Nat. Biotech. 21: 255-261, 2003) Chemical derivatizations can be combined with affinity chromatography to identify specific amino acid modifications. Esterification of negatively charged amino acid residues before immobilized metal affinity column chromatography followed by MS/MS analysis improved identification of phosphopeptides (Ficarro, Nat. Biotechnol. 20: 301-305, 2002). MacCoss used capillary multidimensional liquid chromatography followed by MS/MS analysis to analyze proteins digested with three different proteolytic enzymes and obtained sequence results for overlapping peptides, which reduced ambiguity in mapping modifications, and detected phosphorylation sites (MacCoss et al., PNAS 99: 7900-7905, 2002). Claverol et al. used a strategy combining gel separated proteins and ESI-MS/MS to determine phosphorylation and saccharidic motifs of casein (Claverol, et al., Mol. Cell. Proteomics 2: 483-493, 2003). Chemically induced protein modifications from toxin exposure were identified using a combination of MALDI-TOF with targeted LC-MS/MS (Person, et al. Chem. Res. Toxicol 16: 598-608, 2003).

Cagney noted their experimental results were typical of peptide MS/MS experiments in that long but incomplete y-ion series were observed (Cagney and Emili, 2002). Most de novo peptide MS/MS spectra are either incomplete, or too complicated to be accurately interpreted for sequencing peptides. This is mainly due to difficulties of directionality (distinction of N-terminal ions from C-terminal ions), low efficiency of fragmentation, internal fragmentation, the presence of different types of ions generated during fragmentation (i.e. types b, y, a, c, x and z), the presence of incomplete set of ions of the b and y series, and their tendency to lose $NH_3$ and $H_2O$ groups. These various fragmentation ions can be generated at greatly varying amounts, each with a characteristic ability to be detected in the mass spectrometer. Thus, MS/MS spectra of polypeptides can present as a highly complex series of apparent masses present at greatly varying intensities. Due to the inherent complexity of MS/MS spectral appearance, de novo peptide sequencing has not fully been enabled for polypeptide sequence determination. The presence of sequence errors and compounding factors such as polymorphism, differential splicing, or protein post-translational modifications generate a need for effective de novo sequencing strategies (Cagney, 2002). There would be great advantage to proteomics if the sequence of peptides could be sequentially determined directly by MS/MS spectral analysis.

Attempts at de novo sequencing have focused on addressing the technical difficulties of directionality and labile peptide bonds to simplify or enhance the spectral readout while maintaining accuracy of amino acid definition. Additionally, not all peptides can be resolved due to inherent chemical structure and varied propensity to fragmentation during MS analysis. Several amino acids pose specific difficulties, e.g., isoleucine and leucine have identical masses (isomeric); the masses of lysine and glutamine are similar (isobaric) and difficult to distinguish; the amide bonds linking acidic amino acids aspartic acid and glutamic acid to other amino acids are more labile than other amide bonds, imparting a fragility to the peptide at these sites; the amino acid located just subsequent to the N-terminal amino acid tends to be resistant to fragmentation; and histidine and proline are very difficult to analyze, especially proline adjacent to aspartic acid. Given these technical difficulties and the complex data analysis required, it is not unexpected that faulty or incomplete mass spectral analysis would introduce errors in protein sequences in de novo protein sequencing.

Recently, MS/MS based methods including isotopic labeling and chemical derivatization have improved MS spectral readout (reviewed in Cagney and Emili, 2002). The use of $^{16}O/^{18}O$ labeling improves identification of y-ions, but also reduces the signal intensity (Munchbach et al., Anal. Chem. 72: 4047-4057, 2000; Uttenweiler-Joseph et al., Proteomics 1: 668, 2001). An alternative approach involves methyl esterification of the carboxyl groups in a peptide (Hunt, et al., PNAS 83: 6233, 1986; Goodlett, et al., Rapid Commun. Mass Spectrom. 15: 1214, 2001.) This reaction increases the mass for aspartic and glutamic acid carboxylic side chains, and also modifies the C-terminal carboxyl group. However, for both isotopic labeling and methylation, the modified spectra must still be compared with the original, underivatized peptide spectra. Accordingly, that chemical labeling of peptides may require additional experimental and computational steps that may slow down high-throughput sequencing. Mass spectrometry (MS) involves the analysis of ionized analytes in a gas phase using an ion source that ionizes the analyte, a mass analyzer that measures the mass-to-charge (M/Z) ratio of the ionized analytes, and a detector that registers the number of ions at each m/z value. The MS apparatus may also be coupled to separation techniques to improve the ability to analyze complex mixtures. Further, MS instrument combinations can be made to enhance sensitivity and selectivity. A wide range of MS instruments are available for use in protein sequencing. Regarding ion source, electrospray ionization (ESI) and matrix-assisted laser desorption/ionization (MALDI) are two commonly used techniques to ionize the proteins or peptides for analysis. ESI ionizes the analytes from a solution and MALDI desorbs and ionizes the sample, using a "matrix" that encourages desorption and ionization when exposed to light energy. MALDI produces predominantly singly charged ions from peptides. As described in more detail below, tandem MS/MS is a technique that uses at least two MS components and is a commonly used methodology for MS analysis of polypeptides.

Mass spectrometry (MS) involves the analysis of ionized analytes in a gas phase using an ion source that ionizes the analyte, a mass analyzer that measures the mass-to-charge (M/Z) ratio of the ionized analytes, and a detector that registers the number of ions at each m/z value. The MS apparatus may also be coupled to, separation techniques to improve the ability to analyze complex mixtures. Further, MS instrument combinations can be made to enhance sensitivity and selectivity. A wide range of MS instruments are available for use in protein sequencing. Regarding ion source, electrospray ionization (ESI) and matrix-assisted laser desorption/ionization (MALDI) are two commonly used techniques to ionize the proteins or peptides for analysis. ESI ionizes the analytes from a solution and MALDI desorbs and ionizes the sample, using a "matrix" that encourages desorption and ionization when exposed to light energy. MALDI produces predominantly singly charged ions from peptides. As described in more detail below, tandem MS/MS is a technique that uses at least two MS components and is a commonly used methodology for MS analysis of polypeptides.

Chemical modification of the N-terminus of a peptide before MS analysis has been found to improve MS analysis. The incorporation of a quaternary ammonium group at the N-terminus using the reactive N-hydroxysuccinimidyl ester enhanced sensitivity in MALDI MS (Bartlet-Jones, et al., Rapid Comm. Mass Spectrom. 8: 737, 1994). Cardenas, et al reacted peptides with N-succinimidyl-2-(3-pyridyl)acetate, followed by liquid chromatography separation and analysis by ESI-MS/MS (Cardenas, et al., Rapid Comm. Mass Spectrum. 11:1271-1278, 1997). This reaction modified the N-terminal amino acids and the amino group of lysine. Keough et al. reported the addition of a sulfonic acid group to the N terminus of tryptic peptides increases fragmentation sensitivity and produces much higher fragment ion yields than native peptides. (WO 02/08767; 2003/0032056; WO 02/095419; PNAS 96: 7131-7134, 1999; Rapid Commun. Mass Spectrom 15: 2227-2239, 2001). Destabilization of amide bonds by protonation of amide nitrogen produced extensive fragmentation under MALDI and ESI ionizing conditions (AP MALDI in combination with ion trap MS). The MS/MS spectra of sulfonized peptides containing aspartic, glutamic and oxidized methionine showed more uniform fragmentation along the peptide backbone. Additionally, Keogh, et al. observed the preferential fragmentation on the N-terminal side of proline residues, enhancing recognition of proline.

Chemical modification of the C-terminal amino acid of the peptide before analysis has been found to form longer, more stable series of y-ions. Several methods of C-terminal chemical modification have been reported for lysine. As noted above, trypsin digestion is routinely used in polypeptide analysis by MS to produce fragmentation because the resulting fragment will reliably end in arginine (R) or lysine (K), thus establishing the C-terminal moiety. Although arginine is known to produce an exceptionally strong MS signal, lysine can be difficult to detect. However, lysine can be chemically modified to improve its signal (see Peters, WO 03/056299). This modification distinguishes the mass of lysine from that of glutamine. Cagney and Emili (2002) used a similar approach by differential guanidination of C-terminal lysines followed by LC-ESI-MS/MS analysis (Cagney and Emili, Nat. Biotech. 20: 163-170, 2002). Gu et al (Gu et al., J. Am. Soc. Mass Spectrom. 14: 1-7, 2003) utilized a method incorporating deuterium-labeled (heavy) lysine.

Peters et al. (Peters, et al., WO 03/056299) described a different chemical derivatization method for C-terminal lysine and demonstrated that when the polypeptide's C-terminal lysine was modified by a particular class of reagents, for example 2-methoxy-4,5-dihydro-1-H-imidazole (referred to as "imidazole"), the complexity of the resulting MS/MS spectra was greatly reduced. Peters et al. noted that the y-ion series identification was improved thereby permitting assignment of amino acid sequences more accurately.

Simplification of MS/MS spectra by chemical derivatization of peptides, and the subsequently improved ability to identify the amino acid sequence data, illustrates the potential for developing high quality fragmentation spectra, obtaining long series of complete b, and especially y-ion series, and offers a practical approach to de novo sequencing. An improved resolution in de novo mass measurements increases the accuracy of sequence determination, and decreases reliance on predictive in silico sequence analysis of proteins. However, while chemical modification can increase the reliability and utility of MS analysis and improves the capability for de novo sequencing, several uniquely problematic technical challenges have not been solved and numerous biologically important characteristics of peptides cannot currently be elucidated by existing MS techniques. Moreover, the reliance on computer databases for peptide sequences and protein identification always involves predictions and approximations rather than experimental data, and thereby, increases the possibility for error that cannot be detected from the data. Therefore, ideally, the mass analysis of polypeptides would permit an accurate and reliable polypeptide sequence that would utilize a de novo identification of each amino acid in the peptide.

Given the inherent complexity of peptide fragmentation and the difficulties of MS spectral analysis, a combination of different methods for chemical derivatization of peptides has not been completely developed. For proteomics and analysis of complex mixtures of peptides, it is accepted that only very simple and extremely efficient chemical derivatization steps are compatible with proteomics. If any heterogeneity is introduced by the chemical reaction, the peptide samples become even more complex, thereby complicating the MS analysis and subsequent data processing. (Mann and Jensen, Nat. Biotech. 21:255-261, 2003). Therefore, although chemical derivatization is a known procedure for use in mass spectrometry, the use of multiple discrete derivatization techniques would be expected to introduce significant complexity and complication to a peptide mass analysis and the use of de novo sequencing for a complete determination of the linear amino acid sequence of a peptide is still difficult.

SUMMARY OF INVENTION

The present invention is a novel approach to chemical derivatization of polypeptides for analysis by mass spectrometry. The invention includes both methods and compositions of matter and specifically encompasses chemical derivatives, the serial use of these in concert with MS instrumentation, improved data analysis techniques applied to serially derivatized polypeptide methods for determining the amino acid sequence of specially modified peptides, and methods and apparatus for the use of all of the above in mass analysis. In certain embodiments, the invention also enables new techniques for MS data analysis using spectral data, computer databases, and software and algorithms that use experimental MS data to identify proteins, identify peptides or sequences of peptides, and that perform de novo sequencing of polypeptides.

The benefits of the invention are derived from an increase in the quality of peptide sequencing data based on improvements in the quality of the mass measurements and the intensity and quality of spectral data that identifies amino acids by their mass. This data obtained pursuant to the invention conveys critical information on the mass of peptides and provides both a qualitative and quantitative improvement in MS spectral information and enables analyses that are qualitatively and quantitatively superior to existing techniques and enable the de novo sequencing.

The improvements and advantages of the invention results from serial derivatization of polypeptides using chemical functional groups and reaction techniques that are specially selected and designed to yield improved spectral data using tandem MS. The serial derivatization advances the ultimate goal in de novo sequencing by tandem MS of favoring one type of ion fragment series yielding an approximately equal probability of each amino acid residue yielding a measurable ion. This improvement in data quality is particularly important when performing mass analysis of polypeptides that are known to be problematic for both mass measurement and sequencing based on their amino acid composition, sequence, or post-translational modification. Uniquely problematic polypeptides frequently feature the acidic amino acids, aspartic and glutamic acid residues, because the amide bonds between these residues and their adjacent residues in a polypeptide are inherently more likely to fragment.

Accordingly, with these and other problematic sequences, unpredictable fragmentation patterns occur upon ionization of peptides containing these species. Another inherent problem is the amino acid proline, because this residue has a unique conformational structure that fragments readily, complicating data acquisition for sequences adjacent to the proline residue.

These problematic examples cause significant hurdles in the MS-based sequencing of polypeptides because each instance of uncertainty in assigning an identity to an amino acid residue introduces uncertainty into any subsequent sample analysis, such as the determination of protein identity or comparison of experimental data with a proteomic database. For these reasons, the improvements provided by the invention to the quality of spectral data translate into tangible and practical improvements in protein research.

Because the serial derivatization of the invention provides advantages in the fragmentation properties of serially derivatized polypeptides, distinct qualitative and quantitative improvements in mass spectra are achieved. The significant improvement in mass spectral features, and specifically, the simplification of the appearance of the MS/MS pattern is manifested in several ways. Because of the increased predictability in the fragmentation of the amide bond, individual amino acid residues are more readily detected and the mass values are determined with greater accuracy and certainty. Also, the ability to detect the mass values for a greater number of residues increases the overall quality of the spectra because this improvement yields an identification of the individual residues in a larger piece of a polypeptide sequence.

Another aspect of the improved quality of the MS spectra is the improved signal to noise ratio: on a quantitative basis the ratio is increased simply due to the production of greater signal for individual residues. Qualitatively, the invention yields more peaks from which mass measurement data can be read, whereby the absolute quantity of sequencing ions is increased compared to non-sequencing ions. In practice, ions which result from side chain fragmentation, water ions, and other noise signals are reduced. Reduction of non-sequencing ions provides a significant advantage in spectral quality because many non-sequencing ions have similar mass values to legitimate sequencing ions and the presence of the former introduces uncertainty and potential error into the polypeptide sequence determination. Taken together, all of these aspects contribute to reducing gaps that ordinarily appear in spectral data.

In terms of the quality of appearance of the spectra, a larger number of intermediate peaks are observed and a greater capability is created to identify a sequence of y-ion peaks identifying particular peptides or discernable combinations of peptides. Another benefit provided by improved spectra is an ability to perform a mass analysis at reduced fragmentation energies. Thus, the improved reliability of fragmentation events, ion detectability, and signal to noise ratio of the invention can, in turn, favorably alter the analytical parameters of the instrumentation used in the MS analysis. The capability to reduce the fragmentation energies, in and of itself, also improves the spectra by reducing the non-productive ion fragmentations.

In preferred embodiments, the invention is comprised of at least two chemical reaction steps wherein each is a derivatization of a unique moeity present in a polypeptide. This process is referred to as serial derivatization because two distinct labeling methods are performed. The chemical reaction steps performed in the laboratory can be performed in series or in parallel under the circumstances where the chemical reactions do not interfere either in modification of the peptide or in cross-reaction between reagents, in such a way that compromises the reaction or the derivatization of the analyte peptide. Serial derivatization is typically performed on a sample that has been or will be subjected to digestion to yield polypeptide fragments and typically has at least two discrete chemical labelling steps: in a first step, polypeptides are derivatization following a digestion to establish a reactive terminus and to achieve a first derivative to assist in identification of individual residues. An example of a first derivatization step is a lysine derivatization such as the approach described by Peters, et al. (WO 03/056299). In a second derivatization, polypeptides that have been derivatized by the first derivatization step, such as those derivatized at the lysines, including particularly the C-terminal lysines, are subjected to a second chemical derivatization that uniquely modifies a separate moeity from the first derivatization. An example of a second derivatization is the alkylation of carboxyl groups, for example a methylation of carboxyl groups of aspartic acid residues. The method of performing two unique derivatizations of peptide moieties is distinguished from the use of nuclear isotopes as mass tags or the use of two step chemical reactions that feature the use of protective groups that shield specific peptide moieties from a single chemical derivatization.

The description of serial derivatization is described here as a two step process because the two unique derivatizations are made. The singular derivatization steps described herein could be performed in any order or simultaneously as noted. Because the derivatization of lysine may occur following enzymatic digestion or chemical fragmentation of the polypeptide, this derivatization step may advantageously be performed either first or second in order depending on the analyte or other experimental parameters.

In a preferred embodiment, tryptic digestion of a polypeptide or protein sample is followed by a first derivatization that preferably labels a C-terminus residue of the tryptic fragment, typically the creation of an imidazole derivative of C-terminal lysines. The first or single derivatized polypeptide is reacted with a second derivatizing agent to yield an additional derivatization of polypeptide acidic residue sidechains at carboxyl groups. As noted above, a preferred embodiment of the invention comprises the combination of a first derivatization technique based on the technique of Peter, et al. (WO 03/056299) followed by a second derivatization comprising a methylation of carboxyl groups on the acidic residues. Because the techniques of Peters et al. tends to focus the fragmentation of a polypeptide analyte around the acidic residues, a second derivatization then helps resolve spectral data for the acidic residues and has a synergistic effect in improving the overall quality of the spectra.

The advantages offered by the present invention translate into increased utility of MS data when using hypothetical or actual protein sequences and protein identity databases. Each additional reliable amino acid residue that can be identified increases the accuracy of protein sequencing and protein identification and improves the ability to compare an experimentally-determined sequence with the members of a genomic or proteomic database.

Another application of the improved spectral data enabled by the present invention is to identify variants or modifications of a protein or polypeptide analyte present in a sample. Many important physiological conditions are caused or accompanied by a modification of a protein or polypeptide that may be detected in a biological sample such as blood, urine, saliva, cerebrospinal, fluid, ascites, plasma, cell or tissue samples or extracts or other substance commonly used in analytical methods that contains a polypeptide derived from a patient. With these samples, an accurate experimental measurement of a protein or polypeptide analyte permits analysis and diagnosis based on a comparison of a measured mass spectral pattern of a polypeptide with a hypothetical or standard mass spectral pattern. The standard spectral pattern may represent either a normal analyte or an analyte that is known to represent a disease state or a known physiological condition, or a particular genotype of interest. In this embodiment, an experimentally derived sequence is compared to a standard or reference and the difference is correlated to a specific modification or alteration existing between the standard or reference and the patient analyte. The measured differential thereby identifies a mutation, polymorphism, splice rearrangement, deletion, substitution, or other post-translational modification such as phosphorylation, acetylation, oxidation, methlylation, gelation, glycosylation, etc.

The invention is suitable for use with many types of mass analysis apparatus.

DESCRIPTION OF FIGURES

In FIG. 1B, the spectra of the serially derivatized peptide has a better y-ion intensity distribution thereby facilitating the identification of each amino acid in the sequence.

DETAILED DESCRIPTION OF INVENTION

Figure 1A:
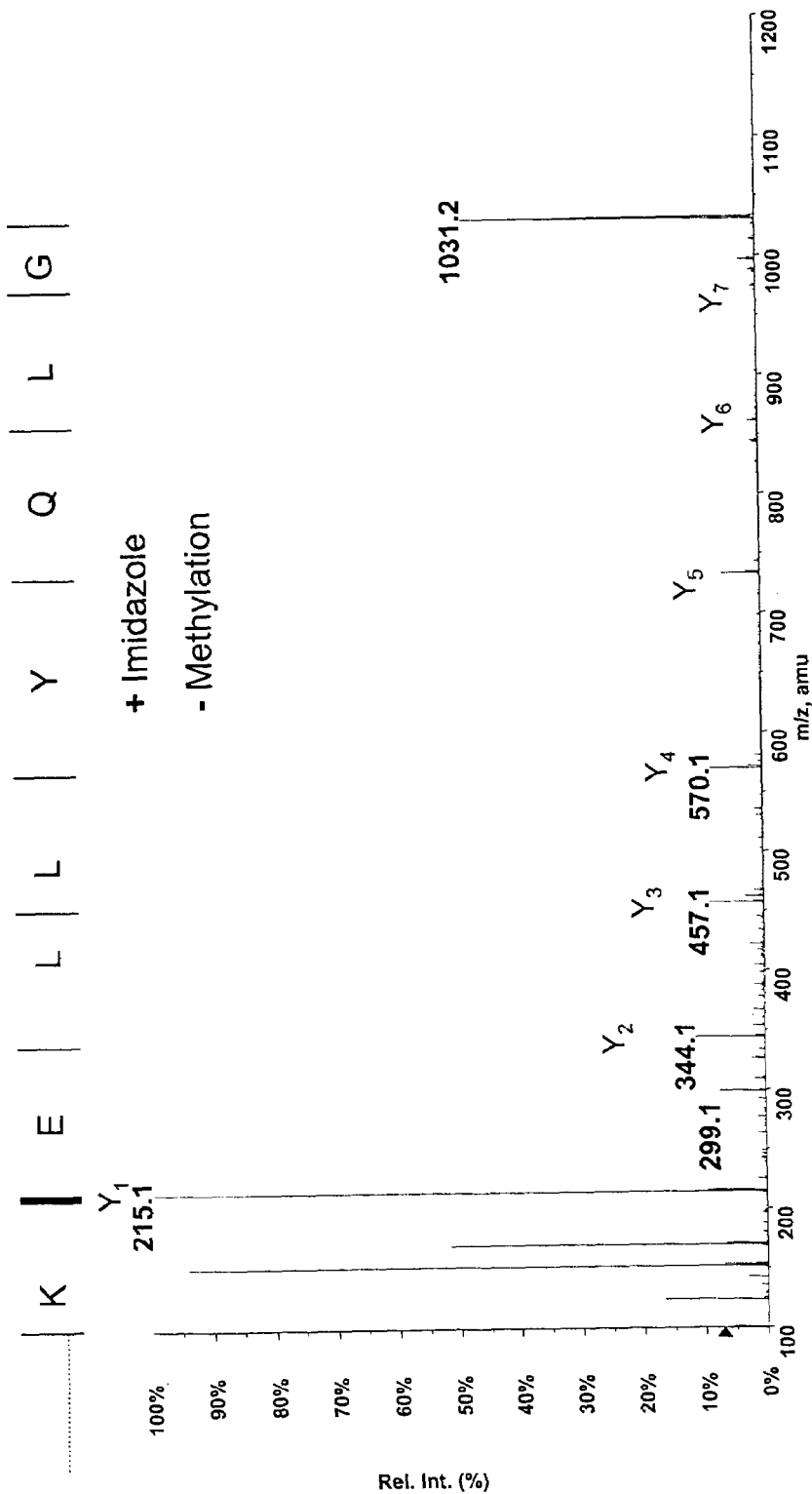
FIGS. 1A and 1B are MS/MS spectra (MALDI/Q-TOF) of imidazole labeled peptide (SEQ ID NO: 1) GLQYLLEK that has been derivatized at the lysine residue by the techniques of Peters et al. (WO 03/056299) and with methylation of carboxylate groups. Peptide (SEQ ID NO: 1) GLQYLLEK was generated from tryptic digestion of beta crystallin (bovine eye lens). The y1 ion and its fragments, i.e. 215.1, 170.1 and 152.1 a.m.u. are dominant in the spectra and therefore suppressed the other y-ions, especially those at higher mass. This could result in the missed identification of amino-terminal residues of the peptide.

Definitions:

As used herein, the terms "alkylating agent" refer to a compound capable of reacting with the carboxylate group of an amino acid to yield an alkyl group derivative as described herein.

The terms "mass analysis" refer to a process wherein the identification of an amino acid residue is determined by measurement of the mass to charge ratio (M/2).

Polypeptide refers to a polymer comprised of amino acid residues, related naturally occurring structural variants, and synthetic non-naturally occurring analogs thereof linked via peptide bonds, related naturally occurring structural variants, and synthetic non-naturally occurring analogs thereof. The term polypeptide also includes a plurality of amino acids existing as a cleavage, digestion, or fragmentation product of a larger polypeptide, wherein the cleavage, digestion, or fragmentation occurred by chemical, biochemical, ionization, mechanical or other reaction. The term "protein" typically refers to large polypeptides. The term "peptide" typically refers to short polypeptides.

The present invention relates to an approach to improve the quality of peptide MS/MS spectra, so that peptide sequence and possibly certain post-translation modifications, can be directly determined without prior knowledge of genomic information. As noted above, mass spectrometry methods for protein identification and sequencing are widely practiced in the field of proteomics. Mass spectrometry can define the characteristic of a polypeptide sequence or to determine differences between two forms of a protein or a polypeptide sequence. A comparison of protein expression from two biological conditions, e.g., from cancerous versus normal cells, can lead to the discovery of a protein or set of proteins that are unique to the cancerous state. The ability to use mass spectrometry in proteomics to obtain de novo sequence information requires highly accurate MS techniques, reliable generation of MS/MS spectra, and the ability to interpret peptide fragmentation to thereby yield a large number of specific residue identifications leading to sequence information that is truly reliable. To achieve this, several known problems in the use of MS data to determine the sequence of peptides must be overcome. Pursuant to this invention, polypeptides are serially derivatized to manipulate the fragmentation characteristics such that y-ions in the resulting MS/MS spectra exhibit more nearly equal intensities with minimal gaps and non-sequencing data points.

An important parameter in de novo sequencing includes the directionality of fragment ions of polypeptide fragment ion charge retention on the amino (b-ion) or carboxyl (y-ion) terminus. Once directionality of fragment ion orientation is assigned, peptide sequence may then be derived de novo by determining the mass for a particular amino acid residue. The de novo sequence information produces an extended, reliable identification of individual residues corresponding to a greater part of the entire peptide and enhances the analysis capability when de novo data is used in database searching. The comparison of sequences derived de novo to those found by database searching, but can also be used to analyze the difference per se between experimental and theoretical data. Where the de novo sequence differs from the sequence derived by database searching, the difference may be attributable to a biological phenomenon that may be identified in the sample, i.e., a biological sample, containing the polypeptide whose sequence is determined experimentally. The specific peptide-based analyses that may be performed are any of those known techniques where a particular molecular form can be determined based on mass. These include phosphorylation, acetylation, oxidation, nitration, methylation, silation, glycosylation, cross-linking, etc. Although specific examples are shown for MALDI/Q-TOF analyses, those skilled in the art can appreciate that this approach is extensible to other MS interfaces (by way of example, electrospray ionization MS), additional MS ionization schemes, fragmentation approaches, and mass spectrometers. For the example chemistry shown, methylation results in the transformation of amino acid side chain carboxyl groups in the C-terminal lysine imidazole-derivatized peptides. The removal of carboxylate group ionic charge could increase the energy required for breaking the adjacent peptide bonds during fragmentation, and thereby, produce MS/MS spectra with improved y-ion intensity distributions. The ability to manipulate the sample to encourage particular fragmentation characteristics greatly simplifies the de novo sequence identification (i.e., the "calling" of the linear amino acid sequence).

The present invention improves post-sequencing analyses of peptide data derived from the serially derivatized polypeptides enabled by the disclosure herein. In some cases, the present invention improves the quality of post-sequence data analysis that can be performed. In other cases, the improvement in spectra data quality enables novel techniques that are not currently achievable due to the inherent difficulties in conducting mass analysis of peptide sequences.

The current invention may simplify sequence interpretation sufficiently to permit automated analysis, for example by the development and use of computer algorithms for automated peptide de novo sequence calling, as well as for post-translational modification identification, and for the application of these methods for high throughout proteomics analysis.

The present invention demonstrates the methylation of acidic residues, combined with the C-terminus lysine derivatization, and subsequent mass spectral analysis. Those skilled in the art can envision additional chemical modifications, at the acidic residue side chains, or elsewhere in the polypeptide chain, at various functional groups, in order to generate improvement in de novo sequence calling accuracy. Similarly, this invention is not limited to claiming greater benefits by the use of a particular serial chemical derivatization method, but also includes the potential to design mass spectral instrumentation to take advantage of this chemical derivization scheme, for example by optimizing for particular fragmentation schemes resulting from serial derivatization.

Although the serial derivatization species and techniques are specially designed to facilitate de novo polypeptide sequencing using tandem MS/MS, their application extends to any mass analysis where information derived from mass from a polypeptide is improved by serial derivatization as described below. Also, although certain techniques are described as preferred, for example the derivatization of lysine and the alkylation of carboxyl groups in acidic residues, numerous other derivatizations are contemplated. Of course, the designation of a specific derivatization as either the "first" or "second" in series may be completely arbitrary, and the term "serial" should not be interpreted to exclude simultaneous labelling of two discrete chemical moeities on a polypeptide if reaction conditions permit.

The use of the an isotope tag to yield an isotopic analogue of the species is not considered a derivatization step of the present invention. Serial derivatization also excludes the use of a single labelling species together with a protecting group. Under such circumstances, only a single target moiety on a polypeptide is labelled, but the protecting groups distinguish certain chemical environments allowing a differential quantitation based on the presence of a single label.

On the contrary, in serial derivatization, two discrete labelling strategies are used to independently derivatize two moeities of the target polynucleotide, preferably at substantially all of the available sites for two or more labels. A preferred example of a first derivatization is provided by Peters et al. PCT/US02/35581, WO 03/056299, which is specifically incorporated by reference herein in its entirety. Typically, the sample containing an intact protein, protein or polypeptide fragment, or other polypeptide analyte is cleaved by a chemical reaction that breaks the amide bond of the polypeptides.

Although the description herein uses a trypsin digestion for illustrative purposes, other specific digestions are possible, including but not limited to chymotrypsin, endoproteases, Arg C or Lys C, chemical fragmentation methods, such as the cyanogen bromide cleavage, hydroxylamine cleavage, BNPS-Skatole, etc. However, the trypsin (or endoprotease) cleavages are preferred because the resulting polypeptides feature a C-terminal lysine or aginine residue. U.S. Pat. No. 5,821,063 provides digestion methods generally for polypeptides. Of course, the derivatization of lysine residues occurs at both terminal and internal lysines, although the labeling of terminal lysines is particularly valuable for sequencing purposes.

Peters et al. derivatize lysine residues by attaching an imidazole derivative having any of the following formulas:

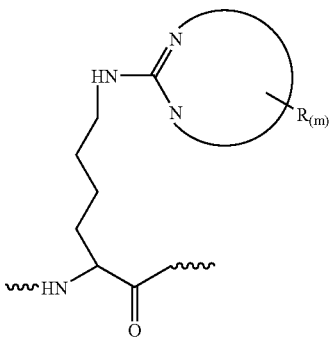

where each R is a functional group independently selected from hydrogen, deuterium, halogen, hydroxyl, cyano, optionally substituted alkyl, optionally substituted alkylcarbamoyl, optionally substituted alkoxy, optionally substituted alkoxycarbonyl, optionally substituted aryl, optionally substituted aryloxy, optionally substituted aryloxycarbonyl, optionally substituted arylcarbamoyl, optionally substituted siloxanly and an affinity tag.

The index "m" is an integer from 0-7, wherein the circle joining the two nitrogens represents an optionally substituted monocyclic or bicyclic ring system having between 2 and 12 additional ring atoms, and wherein the ring atoms are each selected from carbon, oxygen, nitrogen, sulfur and silicon, wherein the foregoing ring atoms are optionally substituted.

In a preferred embodiment of Peters et al., the label has the formula

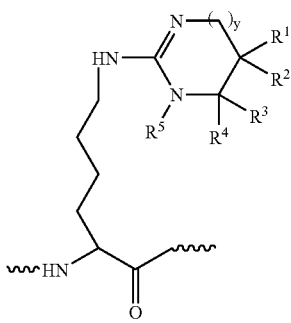

wherein $R^1$, $R^2$, $R^3$ and $R^4$ are each functional groups independently selected from hydrogen, deuterium, halogen, hydroxyl, cyano, optionally substituted alkyl, optionally substituted alkylcarbamoyl, optionally substituted alkoxy, optionally substituted alkoxycarbonyl, optionally substituted aryl, optionally substituted aryloxy, optionally substituted aryloxycarbonyl, optionally substituted arylcarbamoyl, and an affinity tag; or in an alternative embodiment, $R^2$, $R^3$ and the carbons to which they are attached, join to form a n-membered carbocyclic, heterocyclic, aryl or heteroaryl ring, wherein n is an integer from about 4 to about 8. Preferably, a 5-or 6-membered ring is formed. However, in certain embodiments, y is 0, and its adjacent carbon atom together with $R^1$ and $R^2$ are absent, to form a 4-membered ring.

$R^5$ is selected from hydrogen, halogen, hydroxyl, optionally substituted alkyl, optionally substituted alkoxy, optionally substituted aryl and an affinity tag. In Formula I. the index "y" is 0, 1 or 2.

In another embodiment, Peters et al. describe a compound of the formula:

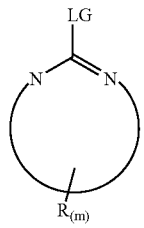

wherein each R is independently a member selected from the group of hydrogen, deuterium, halogen, hydroxyl, cyano, optionally substituted alkyl, optionally substituted alkylcarbamoyl, optionally substituted alkoxy, optionally substituted alkoxycarbonyl, optionally substituted aryl, optionally substituted aryloxy, optionally substituted aryloxycarbonyl, optionally substituted arylcarbamoyl, optionally substituted siloxanly and an affinity tag.

The index "m" is an integer from 0-7, wherein the circle joining the two nitrogens represents an optionally substituted monocyclic or bicyclic ring system having between 2 and 12 additional ring atoms, and wherein the ring atoms are each selected from carbon, oxygen, nitrogen, sulfur and silicon. In Formula II, LG is a leaving group.

In a preferred embodiment, the label has the formula:

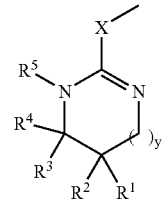

wherein $R^1$, $R^2$, $R^3$ and $R^4$ are each independently selected from hydrogen, deuterium, halogen, hydroxyl, cyano, optionally substituted alkyl, optionally substituted alkylcarbamoyl, optionally substituted alkoxy, optionally substituted alkoxycarbonyl, optionally substituted aryl, optionally substituted aryloxy, optionally substituted aryloxycarbonyl, optionally substituted arylcarbamoyl, and an affinity tag; or, in an alternative embodiment $R^2$, $R^3$ and the carbons to which they are attached, join to form a n-membered carbocyclic, heterocyclic, aryl or heteroaryl ring, wherein n is an integer from about 4 to about 8. Preferably, a 5-or 6-membered ring is formed. However, in certain embodiments, y is 0, and its adjacent carbon atom together with $R^1$ and $R^2$ are absent, to form a 4-membered ring.

$R^5$ is selected from hydrogen, halogen, hydroxyl, optionally substituted alkyl, optionally substituted alkoxy, optionally substituted aryl and an affinity tax. LG is X—CH$_3$, wherein X is a heteroatom such as O and S. The index "y" is 0, 1 or 2.

A particularly preferred embodiment of the above formulas are 2-methoxy-4.5-dihydro-1H-imidazole and a preferred practice of the above derivatization yields an imidazole derivative at the C-terminal lysine residue of polypeptide digested by trypsin.

In addition to the species disclosed by Peters et al., many other derivatizations of polypeptides are known that can be practiced as an element of the present invention. Many of these techniques are known to have selective reaction characteristics and to result in characteristic features observable in an MS/MS spectra. As noted above, the unique difficulty in determining peptide sequences for certain polypeptides arises from the unique chemistry and specific functional groups existing in these polypeptides. Several of these single items may be individually addressed with a variety of single derivatization techniques encompassed within the scope of this invention. Another example is proposed by Caguex et al. using treatment of polypeptide sequences by O-methylisourea, Nature Biotechnology 20:163-170 (2002). However, the added utility in de novo sequencing is based on a qualitative or quantitative improvement in spectral quality. This approach shows an example of a single derivatization of lysine residues as an attempt to improve fragmentation characteristics and mass data that is useful in sequencing data quality.

The first derivatization is not limited to those that focus on labelling of C-terminal residues to yield improvements in predominantly y-ion spectra. Carderas et al. Rapid Comm. Mass Spectrum. Vol. II, 1271-1278 (1997) labelled peptides prior to passage through an LC column and subsequent analyses by ESI MS/MS analysis. The derivatization reaction is performed in a conventional LC apparatus where protein sample was subjected to modified tyrosine digestion and then derivatized in-line with N-succiusmidyl-2(3-pyridyl) acetate (SPA). The resulting pyridylacetyl derivative of N-terminal and lysine side-chain amino groups co-existed with partial labelling of trypsin-OH groups. This technique helps distinguish isobaric residues and an alteration of the CID fragmentation pathway in favor of b-ion formation.

An additional functional derivatization of the N-terminal residues of a peptide is described in Bhikhabbai et al. PCT/US02/16247 wherein an aqueous phase derivatization is achieved with an acidic reagent with a sulfonyl moiety together with an activated acid moiety. The features of this reaction are such that it requires a larger sample size due to its tendency to reduce sensitivity of MS detection. In considering the selection of a derivatization reaction, the ability to cause fragmentation reactions from the C-terminal end of a polypeptide fragment to yield y-ions capable of identifying residues in a sequencing analysis must be balanced against the tendency for such derivatizations to dramatically reduce the sensitivity in the resulting mass spectra. The derivatization of Bhikhabbai et al. may be achieved in combination with a step that protects reaction of certain functional groups that would otherwise be derivatized. The combination of a sulfonyl moeity together an activated acid moiety will cause the sulfonation reactions at each lysine residue. In order to protect lysine residues against this reaction, a protection procedure using a guanination reaction is conducted to specifically protect lysine side chains from reaction in the derivatization step. Such a protecting group reaction is necessary for this species of derivatization in particular where a trypsin digest is used, thereby creating multiple lysine or arginine residues at the C-terminus of the peptide fragment. The combined use of a protecting group and an activated acid moiety together with a sulfonyl moiety is a single derivatization within the context of a serial derivatization as described herein.

An additional single derivatization is described in Keough et al. (WO 00/43792) wherein a derivatization of the N-terminus of a polypeptide with one or more acidic moieties with a pKa value less than 2 is achieved with, for example, a sulfonic or disulfonic derivative. This derivatization attempts to cause selective cleavage of the amide bonds of the polypeptide in a charge-site specific manner to enable selective detection of only y-ions in a single series.

As noted above, the second derivatization step helps to resolve uniquely problematic mass measurements and detects problems in singularly derivatized polypeptides. The example of an alkylation of carboxylate groups in acid side chains is a preferred example and is consistent with the principle of the present invention to alter the fragmentation characteristics of the derivatized peptide to give a predominantly y-ion series with nearly equivalent intensities.

Alkylation of carboxyl groups of acidic amino acid side chains in glutamic and aspartic acid and derivatives and analogues is achieved as described below in Example 1. The alkylation of the carboxyl groups in a peptide helps distinguish y ions from any other ions present including chemical noise. In the preferred example of a methylation, the reaction also increases the mass of the polypeptide fragment by 14 mass units for each carboxyl group. Absence of the acidic side chains of aspartic and glutamic acid, only the C-terminal carboxyl group will be observed to react and exhibit the 14 mass unit shift.

Generally, the alkylation labels the carboxyl groups to form an ester with a straight chain, branched, or tertiary alkyl group of the formula $CH_3(\text{---}CH_2)_n$ when $n=0\text{-}3$ and where the alkyl species may be a methyl, ethyl, propyl, n-propyl, isopropyl, butyl, n-butyl, isobutyl, sec-butyl, or t-butyl species, and where the methyl species is preferred.

The alkylation reaction adds an alkyl group, +14 am's for a methylation, to the carboxyl group of the acidic side chains of proteins. This reaction occurs particularly with aspartic acid, glutamic acid, and S-carboxymethylated cysteine. The reaction causes both mass change corresponding the number of acidic side chains and the species of alkyl group selected and yields the improvement is MS/MS spectra described herein. A digestion or other fragmentation may be performed on both derivatized or un-derivatized polypeptides to locate the acidic residues. Accordingly, as noted above, the term "alkylation" or "methylation" typically refers to forming an alkyl or methyl ester of the carboxyl group, however the reaction might not always result in an esterification and the alkylation can also cause alterations in charge distribution around the carboxyl group that still provide the benefits of the present invention without being strictly limited to formation of the alkyl ester.

As will be appreciated by the foregoing description, the invention also includes methods for: derivatization of peptides, mass analysis of derivatized peptides, determination of amino acid sequence of derivatized peptides, analysis of sequence, and several other specific methods based on the use of data obtained from serially derivatized peptides. An initial step in these methods may include separating and preparing analyte for mass analysis. Typically, this step involves obtaining a sample containing a polypeptide, separating the polypeptide from the sample (although for some samples this step may be omitted), and preparing the polypeptide for the derivatization step by purification, digestion, or otherwise. The analyte is then subjected to the first and second chemical derivatization as described above. The steps may be performed simultaneously if the reactions do not compete or compromise the labeling of the peptide or comprise the structure or chemical composition of the analyte. Once the sample/analyte is prepared, the mass analysis is performed and a spectrum is obtained wherein polypeptide fragments are measured by MS/MS and mass/charge data for the derivatized polypeptides is obtained. The mass spectrum is comprised of data that correlates the mass/charge ratio of peptide fragments to an amino acid sequence and may be comprised of qualitative or quantitative data in any form or format that may be used to assign information about the analyte which includes an amino acid sequence.

In additional to literal sequence data, the spectra may also contain data reflecting non-sequence information regarding the underlying peptide, including chemical information for the peptide, including gylcosylation, hydration, or other chemical modification. Non-sequence information for a first analyte can be used to determine information about the first analyte directly or can be compared with sequence or non-sequence information from a second analyte or from the nature of the samples from which a first or second analyte is obtained. This type of data analysis is particularly useful when comparing the form of two analyte peptides in proteomics analyses.

The specific techniques include measuring the experimental or actual mass of an analyte, determining the amino acid sequence of an analyte, measuring a difference between the experimental or actual mass and a theoretical value based on the molecular weights of the constituent atoms and determining the source of the difference between the experimental values obtain and the theoretical values or known mass data for any polypeptide species.

Mass analysis data or spectra may be used with known sequencing algorithms to yield the amino acid sequence of the peptide analyte (Taylor and Johnson, Rapid Communications in Mass Spectrometry, 11, 1067-1075, 1997; Chen, et al., Journal of Computational Biology, 8(6), 571-583, 2001; Dancik, et al., Journal of Computational Biology, 6, 327-342, 1999; Eng, et al., J. Am. Soc. Spectrom., 5:976-989, 1994; Mann & Wilm, Anal. Chem., 66:4390-4399, 1994). These algorithms are well known and can be used with some degree of utility regardless of the accuracy or precision of the mass analysis data. The improvement in data acquisition and mass spectra quality provided by the present invention increases the utility of sequencing algorithms and increases the accuracy of the sequence information and the length of the sequence that can accurately be determined. The methods of the present invention include applying available sequencing algorithms to the sequence information obtained from mass analysis of serially derivatized polypeptides, and securing sequence information for the uniquely derivatized polypeptides or fragments.

Using accurate amino acid sequence data determined using the present invention, the identification of partial and full length proteins can be made from only an accurate determination of a partial amino acid sequence and a search of a protein database. In many proteomics studies and basic biological assays, the critical determination is an identification of the identity of an analyte protein, sometimes as present in a biological sample. Typically, these proteomics databases operate by aligning an experimentally-determined amino acid sequence against a large number of reference amino acid sequences in a database of full-length proteins and identified protein fragments. As is readily appreciated, an increase in the accuracy of sequence information and in the number of sequences identified in a polypeptide analyte will improve the utility of comparing or identifying experimentally-determined polypeptide fragments against reference sequencing. Accordingly, one aspect of the invention is the use of sequence data obtained from mass analysis of the serially derivatized polypeptides described herein to identify proteins by submitting the amino acid sequence, determined from experimental MS data, to a protein database to identify the analyte and/or to identify the analyte as a component of a sample.

It has been shown that five or more amino acid sequences in series (contiguous sequence with no gaps) can be used to search databases to identify a protein with high confidence (Mann & Wilm, Anal. Chem., 66:4390-4399, 1994). These lengths of amino acid sequence have been referred to as critical length sequence tags. Longer amino acid sequence tag could dramatically increase identification accuracy, which is very useful, when many proteins in the database share certain amounts of evolutionarily conserved sequences. Longer amino acid sequence tags also increase the confidence of protein identification for organisms without fully or adequately sequenced genomes. However, when a gap is found in a sequence tag, (for example, instead of a five consecutive amino acid tag, there is a three amino acid tag plus a gap of variable length, followed by a two amino acid tag), the protein identification becomes very difficult. More proteins can be matched to the smaller sequence tags, and because the directionality of the two small tags is also unknown, the protein identification is very unreliable. Mann and Wilm have proposed that the minimum sequence tag for 85% confident protein identification should be at least three to four contiguous residues, but clearly longer sequence tags are beneficial.

As noted above, the technique of the present invention is particularly useful for the MS/MS analysis of post translational modifications in proteins. These modifications are broadly defined as any alteration in the sequence or chemistry of a polypeptide that occurs after the amino acid sequence has been translated from messenger RNA. Post translational modifications can be particularly important in proteomics analyses and the study of proteins in clinical samples related to disease. Many types of post translational modifications, such as glycosylation, and the others described herein, are known to coincide with particular disease states or may indicate physiological conditions that are clinically important in diagnosis of a patient. In some cases, the ability to improve the mass spectra of a polypeptide fragment using the serial derivatization methods described in the present invention also allows the detection and identification of a specific post translational modification by direct measurement of the mass of a polypeptide analyte and comparison to a reference value. Under these circumstances, the mass analysis is experimentally performed to measure the mass of a polypeptide fragment and that mass is compared with the expected mass of the polypeptide fragment either with or without a post translational modification. For example, the addition of a water molecule as a post translational hydration of a polypeptide fragment would increase the mass by 18, i.e., the mass of the added water molecule. When the mass analysis of a polypeptide fragment yields a number that is 18 units different than the native polypeptide, the post translational modification is identified. A similar analyses can be performed for all types of post translational modifications where a difference in a mass measurement from the native polypeptide compared to the modified polypeptide can be made and where the reference mass number is known.

Similarly, there is considerable significance in the identification of the specific residue within a given peptide sequence which has undergone a post-translational modification. For example, in a peptide which possesses more than one site of potential modification. An example of this would be a peptide sequence that has two potential sites of phosphorylation. In order to identify the unique site of modification, a de novo sequence analysis by MS/MS fragmentation may distinguish between the two potential sites of modification, as the MS/MS fragmentation pattern should exhibit a y-ion shifted by the appropriate mass for the additional mass of the phosphoryl group (80 amu), added to which is the mass of the amino acid residue to which the phosphoryl group is attached. Thus, the MS/MS spectral information includes the amino acyl mass-depended shift, in addition to the mass of any attendant modifications. It is apparent that mass shifts between adjacent y-ions which do not coincide with known amino acid masses, are diagnostic of the presence of a modification, including the known or yet-to-be-known post-translational modification.

A similar capability exists where any difference in mass analysis can be attributed to a disease or any physiological condition of clinical interest. For example, where a protein mutation is known to be responsible for a particular disease state, and where the mutation is known and results in a difference in mass from the native polypeptide, or that polypeptide representing a normal or non-disease state, a clinical diagnosis may be made from the mass analysis by comparing the mass of a polypeptide analyte in a patient sample from the known mass in the native or non-disease state. For such an application, the methodology of the present invention need only be modified to include a step where the polypeptide analyte is separated from a patient sample prior to the serial derivatization as described above. Further, data processing of the mass data or spectra includes the step of determining the mass of at least one polypeptide fragment comprised of a portion of the patient sample and comparing that result with the known mass for the non-disease state. A comparison of the patient and normal samples indicates whether or not the disease state is present. Because the serial derivatization of the present invention enhances the ability of tandem MS/MS to perform de novo peptide sequencing in a high throughput fashion, the invention also increases the utility of the MS/MS technique for clinical diagnosis and large scale screenings for any detection of polypeptide sequences.

As will be apparent to one of ordinary skill in the art, the increased utility of the present invention in polypeptide sequencing also translates into an increased utility in genomics analyses in the use of polynucleotide databases. Any time a polypeptide sequence is known, theoretical polynucleotide sequences can be determined and searches can be made within known databases for similarity with known sequences, i.e., by BLAST or other known techniques. Within the context of the methods of the present invention, the added utility of determining polynucleotide sequences in performing genomics analyses requires only proceeding from the mass analysis of the serially derivatized polypeptide to a determination of the polypeptide sequence, the determination of theoretical polynucleotide sequences by known techniques, and the use of existing polynucleotide databases to correlate the sequence of a polypeptide analyte to the underlying polynucleotide sequence that codes for either the polypeptide fragment or a full length polypeptide containing the fragment.

As with the examples described above for proteomics research, the ability to detect alterations such as mutations or post translational modifications in a protein sample can be coupled to the underlying polynucleotide sequences that code for the protein to perform genomics research based on the sequence of the serially derivatized polypeptide. As in the proteomics application, data from an experimentally obtained polynucleotide sequence can be analyzed for differences between the experimentally-determined polynucleotide sequence and a reference sequence can be identified and correlated to a disease or other physiological condition. In each such application, the fundamental advantage provided by the invention is the comparison of the spectra or mass data generated by mass analysis of the serially derivatized polypeptide with a reference value, either a reference value for the mass of a known polypeptide, or a reference value for the sequence of a known polypeptide. Accordingly, a comparison of the data generated by the present invention may comprise a comparison of experimentally obtained mass data with a database containing reference mass data, or a comparison of experimentally obtained sequence data with a database containing reference sequence data, or a combination of the two.

EXAMPLE 1

Derivatization and Imidazole Peptide and Methylation of Carboxyl Groups

Eight proteins, β-casein (bovine milk), myoglobin (horse heart), cytochrome c (bovine heart), β-crystallin (bovine eye lens), calmodulin (bovine brain), human serum albumin, pyruvate kinase (rabbit muscle) and human transferrin dissolved individually in a buffer contains 8M urea, 100 mM $NH_4HCO_3$, pH 8.5 with final concentration about 2 mg/ml. About 200 μg of each protein were first reduced with tris(2-carboxyethyl)-phosphine hydrochloride at 37° C. for 30 minutes and reacted with iodoacetamide at room temperature for 30 minutes. The resulting protein solutions were then diluted four times with final urea concentration was 2 M, and trypsin was added at 40:1 and incubated at 37° C. overnight. Digestion reaction was quenched by added small amount acetic acid. Cytochrome c and transferrin were reduced and alkylated as described above. Without dilution, Lys-C was added to the protein solution at 100:1 and incubated at 37° C. overnight and quenched with acetic acid.

To modify the carboxy-terminal lysine of peptides with imidazole, tryptic digest of a protein 30 μl (~10 μg) was mixed with 20 μl of 1 M imidazole stock (e.g., 2-methoxy-4,5-dihydro-1H-imidazole at a final concentration of 400 mM). The reaction mixture was incubated at 60° C. for 3 hours and stopped with 5 μl of glacial acetic acid. The peptides were then purified over a C18 spin column (Pierce), divided into two halves and lyophilized. One half was dissolved in 50:50 v/v methanol:water, and analyzed by MALDI-MS/MS. To derivatize carboxylate groups, the other half was dissolved in 100 μl of 2M methanolic HCl, as an alkylating agent, and incubated at room temperature for 2 hours (Ficarro et al., Nature Biotechnology, 2002, 20:301-305). The reaction was stopped by lyophilization. The lyophilized peptide mixture was redissolved in 50:50 v/v methanol:water, and analyzed by MALDI-MS/MS. Eight different proteins were tested individually using this method. As will be appreciated by those skilled in the art, to increase protein sequence coverage of individual proteins or to analyze more complex protein mixtures, such as protein complexes, or even total cell lysates, the derivatized peptides could also be separated by single or multidimensional separation techniques, for example liquid chromatography, then analyzed by a suitable mass spectral method, for example by MALDI-MS/MS, or on-line electropray ionization MS/MS. Representative MS/MS spectra from cytochrome, pyruvate kinase, and β-crystallin are shown.

The improvement in spectral quality with the serially derivatized peptides (the B panels of FIGS. 1, 2, 3, and 4) is dramatic comparing to the corresponding, non-derivatized peptides (the A panels of FIGS. 1, 2, 3, and 4), and peptide sequences can be easily determined from these spectra. In all cases, higher collision energies were required for peptide fragmentation in carboxylate-derivatized peptides than in non-derivatized peptides, an indication of stabilized peptide bonds. The y ions generated by the breakage of carboxylate side chains of acidic residues no longer dominated, such as the y2 ions in panel A of FIG. 2. And, in general, the y1 ion and its fragments are no longer the dominant features in MS/MS spectra. Both improvements allow more high mass y ions to be detected. Overall, the carboxylate derivatized peptides produced fragments on MS/MS spectra with a more complete y-ion series and evenly distributed peak intensity, a desired feature for de novo sequencing.

Figure 1B:
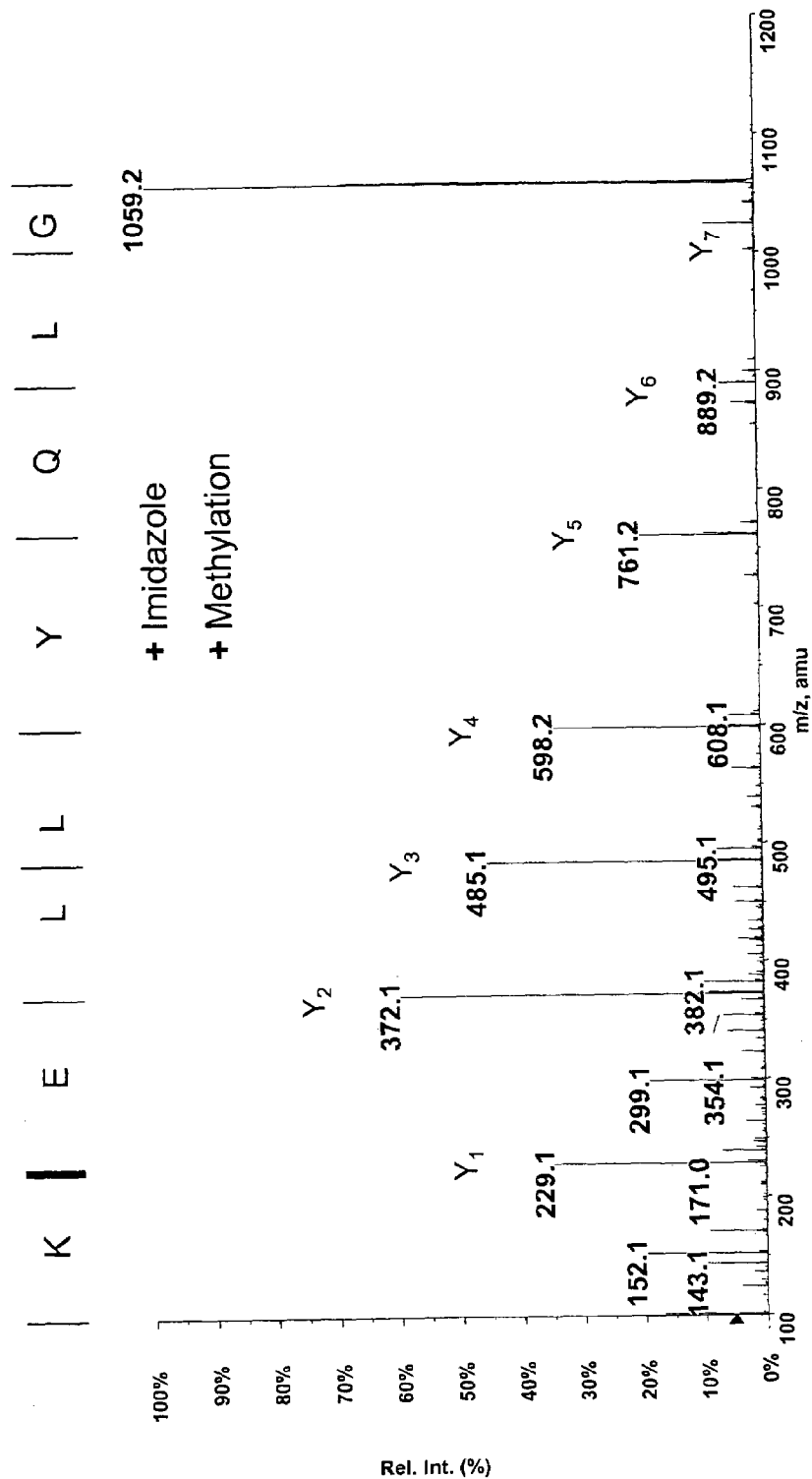

Referring to FIGS. 1A and 1B, FIG. 1A is the MS/MS data resulting from a MALDI/Q-TOF MS analysis of a peptide (SEQ ID No: 1) that has been derivatized at the lysine residue using the approach described by Peters, et al (WO 03/056299). As shown in FIG. 1A, certain features might present problems for directly deciphering amino acid sequenced. The y ion and its fragments, i.e. 215.1, 170.1 and 152.1 a.m.u., are dominant in the spectra and have suppressed other y ions, especially those with higher mass. The suppression of other y ions in the series increases the possibility that amino terminal residues in the peptide will be misidentified. In comparison, FIG. 1B shows a substantially improved y-ion intensity distribution and an improved ability to identify the constituent sequences.

Figure 2A:
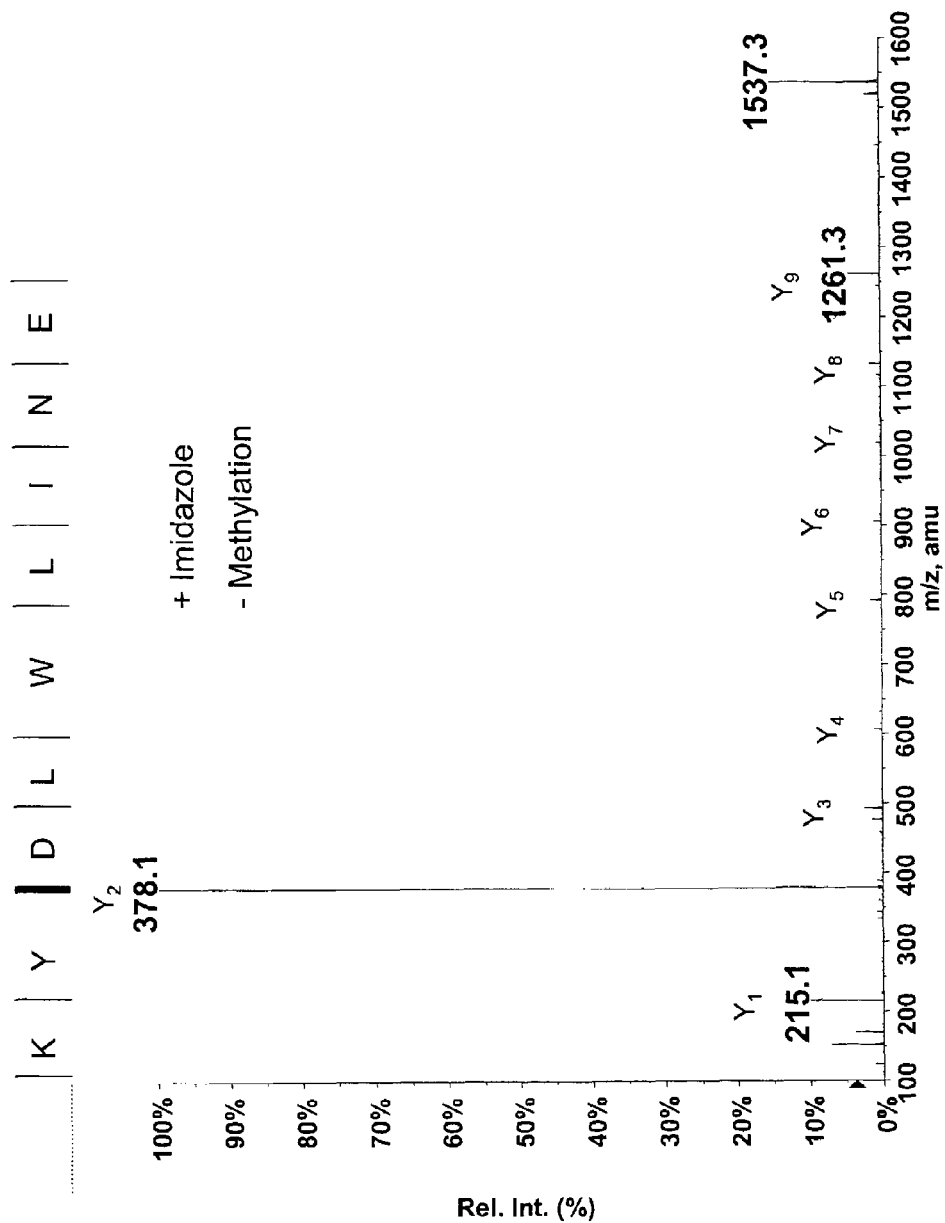
FIGS. 2A and 2B are MS/MS spectra (MALDI/Q-TOF) of imidazole labeled peptide (SEQ ID NO: 2) CDENIL-WLDYK generated from tryptic digestion of pyruvate kinase (rabbit muscle). An additional problem for the analysis of polypeptides is the peptide bond carboxy-terminal to acidic residues, i.e. glutamic acid and aspartic acid, tend to break easily under certain sequence context, resulting in MS/MS spectra with only a few dominant peaks insufficient for determining the full length sequence of the peptide. This case is exemplified by MS/MS spectral data generated by analysis of peptides like those shown in FIG. 2A. The improvement in spectral quality with the serially derivatized peptides (FIG. 2B) is dramatic comparing to the corresponding, non-derivatized peptides and peptide sequences can be easily determined from this spectrum.
Figure 2B:
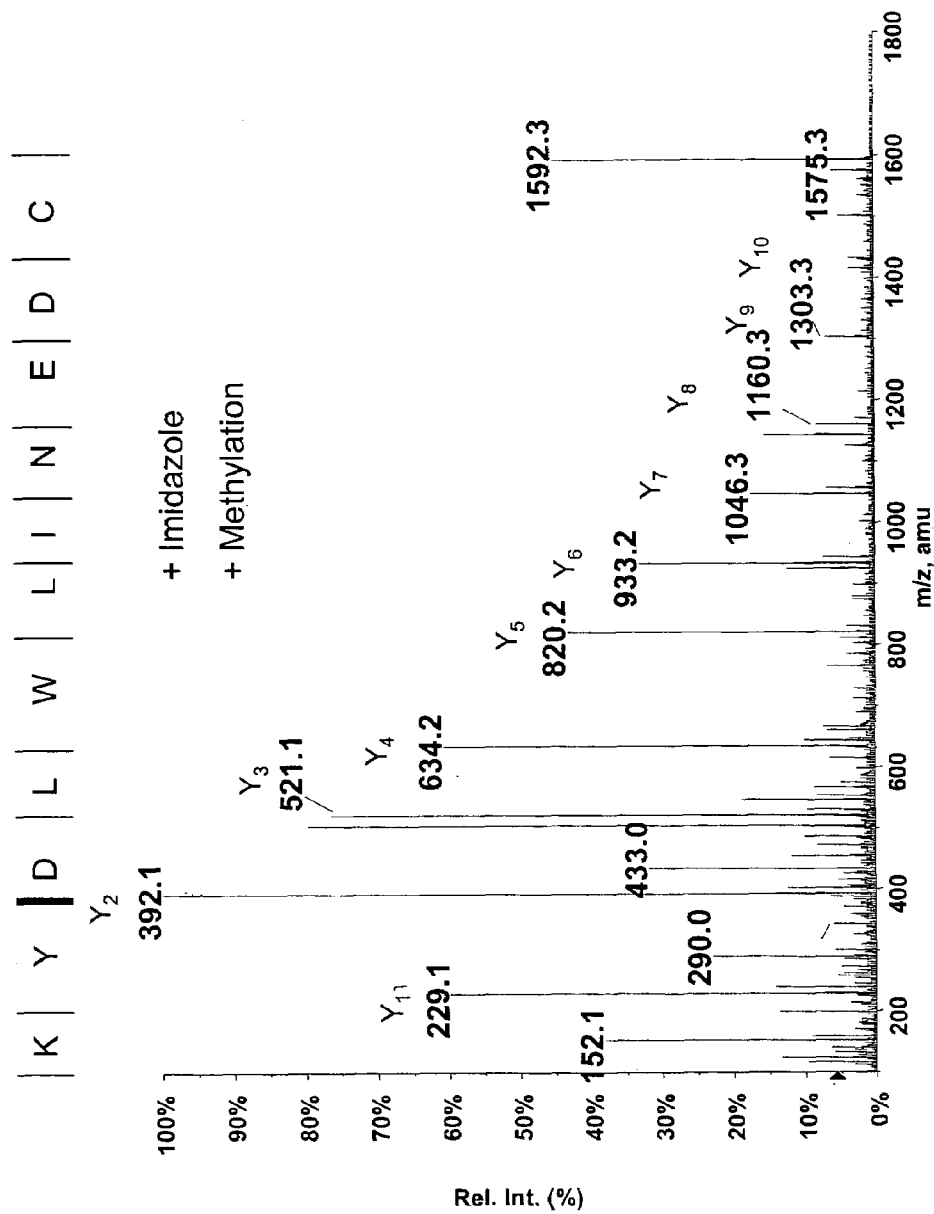

An additional problem can result from analysis of polypeptides in which the peptide bond carboxy-terminal to acidic residues, i.e. glutamic acid and aspartic acid, tend to break easily under certain sequence context, resulting in MS/MS spectra with only a few dominant peaks, insufficient for determining the full length sequence of the peptide. This could result in the missed identification of residues of the peptide. This case is exemplified by MS/MS spectral data generated by analysis of a peptide (SEQ ID No: 2) as shown in FIG. 2A. FIG. 2B shows the improvement in spectrum quality following a methylation at the polypeptide fragment.

Figure 3A:
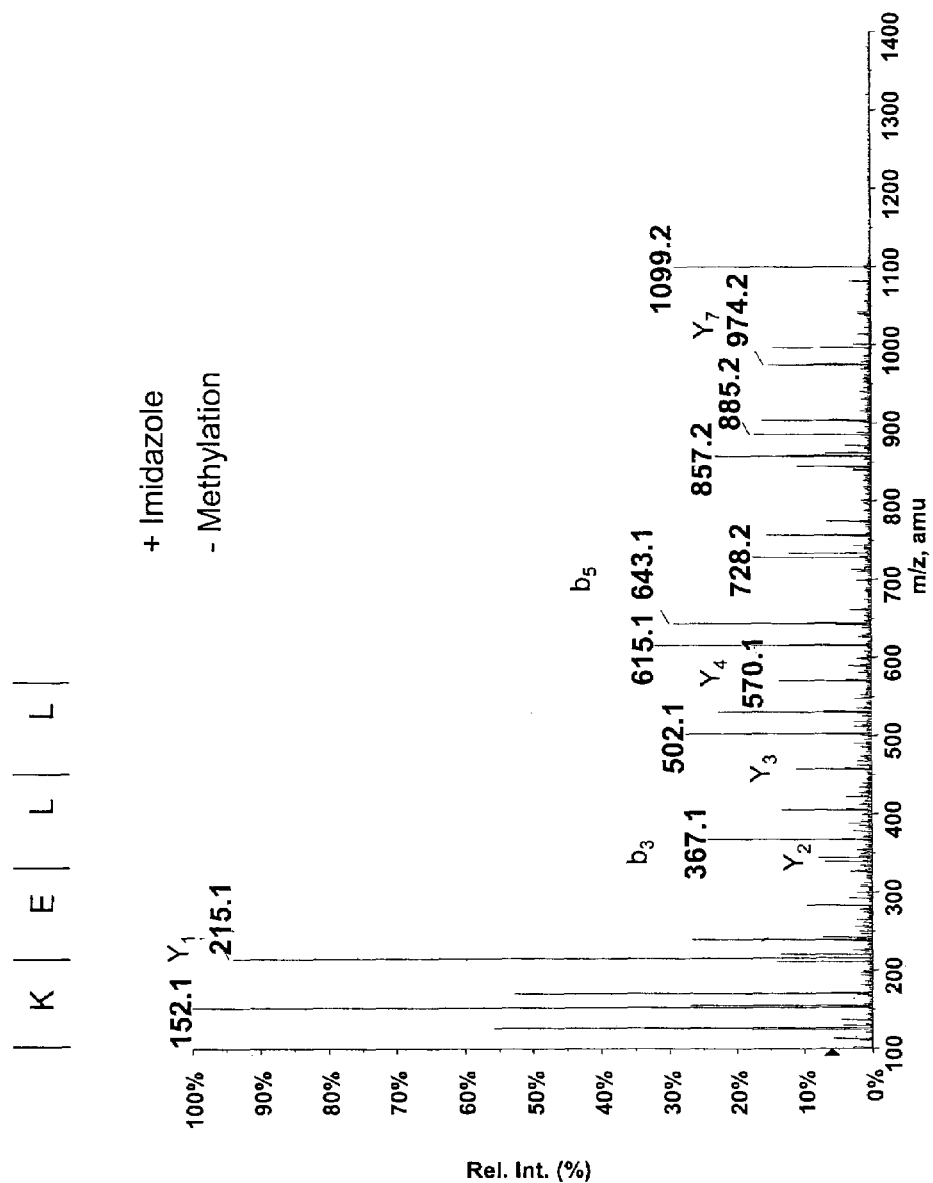
FIGS. 3A and 3B are MS/MS spectra of imidazole labeled peptide (SEQ ID NO: 1) GLQYLLEK when both the carboxy-terminal lysine and the amino-terminal lysine were derivatized with imidazole as per the technique of Peters et al. (WO 03/056299) generated from tryptic digestion of β-crystallin (bovine eye lens). Although the primary amines at the amino-terminal of a peptide usually do not react with imidazole reagent, when the amino acid residue at amino-terminal of a peptide is a glycine, the N-terminus is derivatized at a slower rate. The MS/MS spectra from such double-labeled peptide are difficult to interpret de novo, due to incomplete y-ions series as well as the presence of y, a, b and some c ions. When the same peptide was serially derivatized, the y-ion series becomes the dominant feature in the spectrum and de novo interpretation became much easier and more accurate, as shown in FIG. 3B.
Figure 3B:
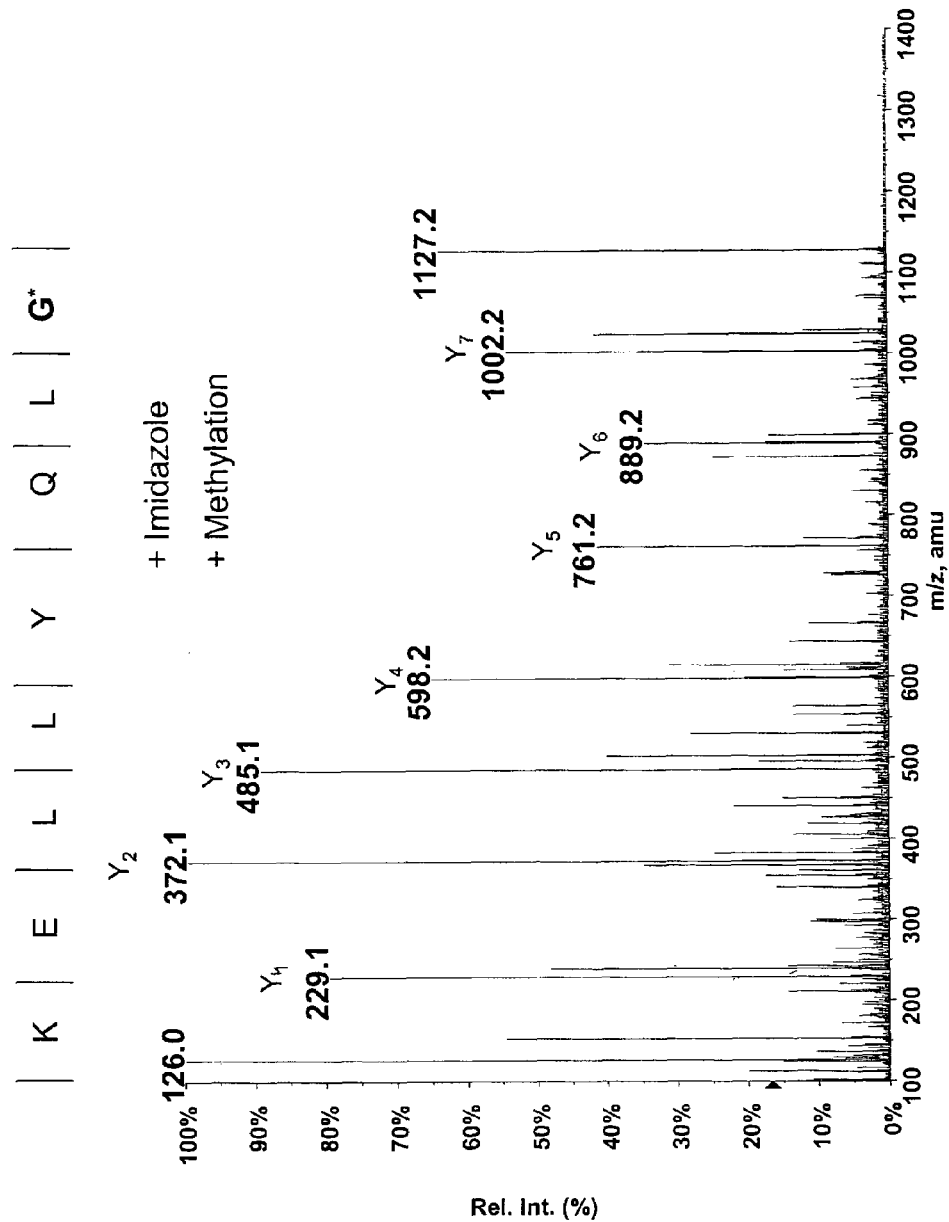

Referring to FIG. 3A the MS/MS spectrum resulting from a peptide (SEQ ID No: 1) where both the carboxy-terminal lysine and the amino-terminal glycine were derivatized with imidazole shows that although the primary amines at the amino-terminal of a peptide usually do not react with imidazole reagent, when the amino acid residue at amino-terminal of a peptide is a glycine, the N-terminus is derivatized at a slower rate. The MS/MS spectra from such double-labeled peptide are difficult to interpret de novo due to the incomplete y-ions series as well as the presence of y, a, b and some c ions. When the same peptide was serially derivatized pursuant to this intention, the y ion series becomes the dominant feature in the spectrum and de novo interpretation became much easier and more accurate, as shown in FIG. 3B.

Figure 4A:
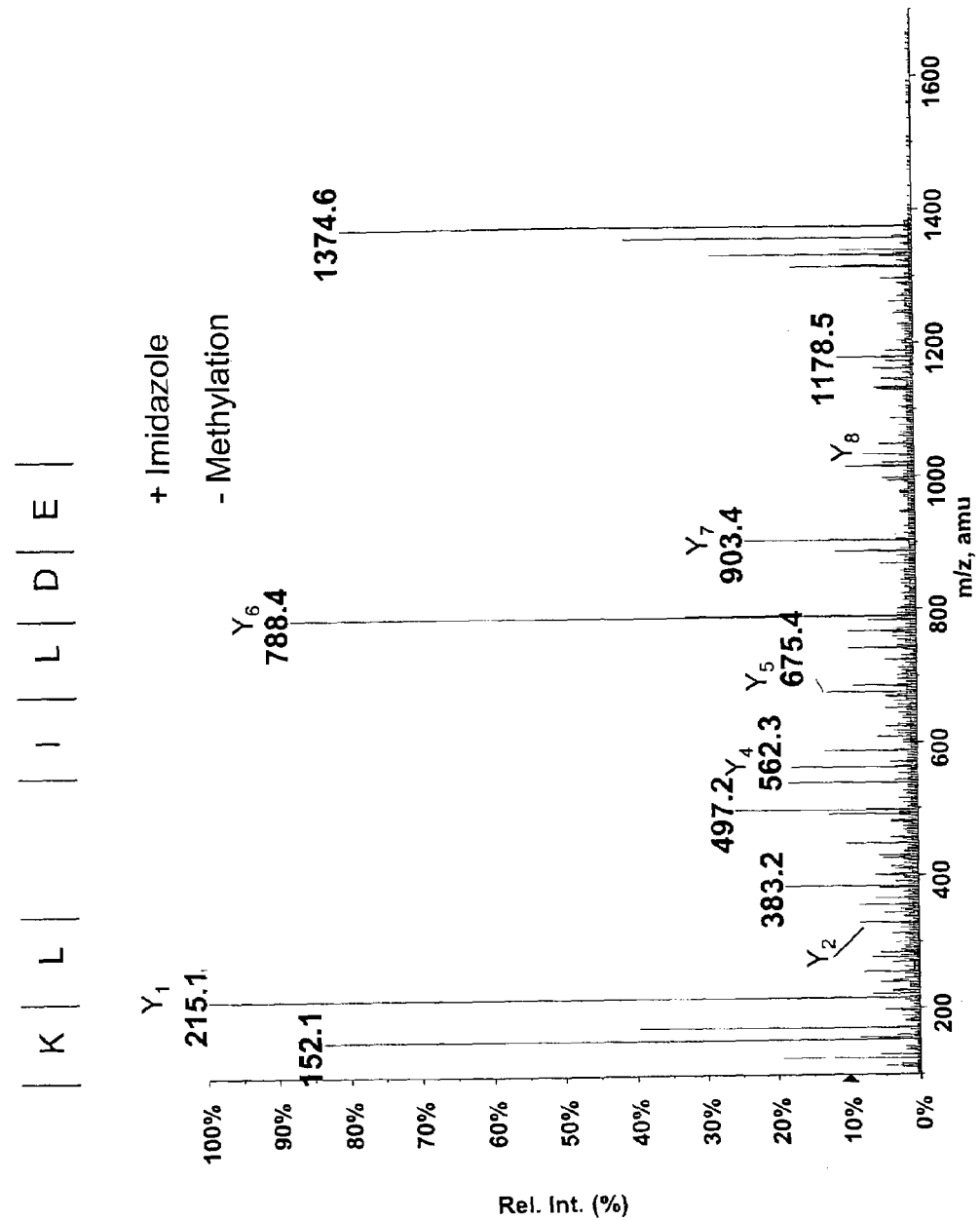
FIGS. 4A and 4B. Lys-C can be used to digest proteins to increase carboxy-terminal lysine occurrence, which could increase protein sequence coverage for identification. However, the resulting peptides after Lys-C digestion often have internal arginine, which make their MS/MS spectra difficult to interpret even after imidazole derivatization as shown in FIG. 4A. The MS/MS spectrum of serially derivatized same peptide from cytochrome C (bovine heart) (SEQ ID No: 3) (FIG. 4B) shows a long dominant y-ion series up to the internal arginine, permitting a read out of a long stretch of the peptide sequence.
Figure 4B:
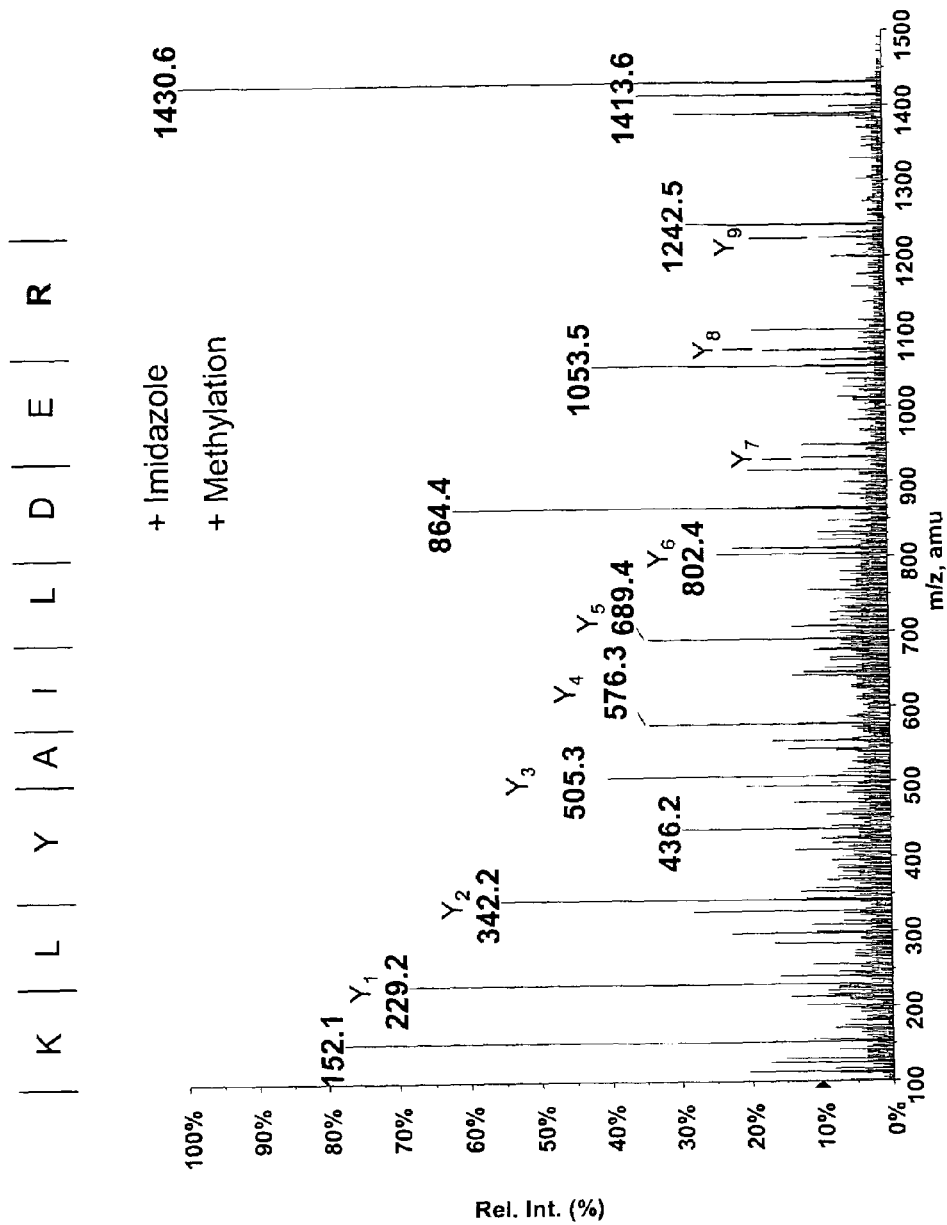
Figure 5:
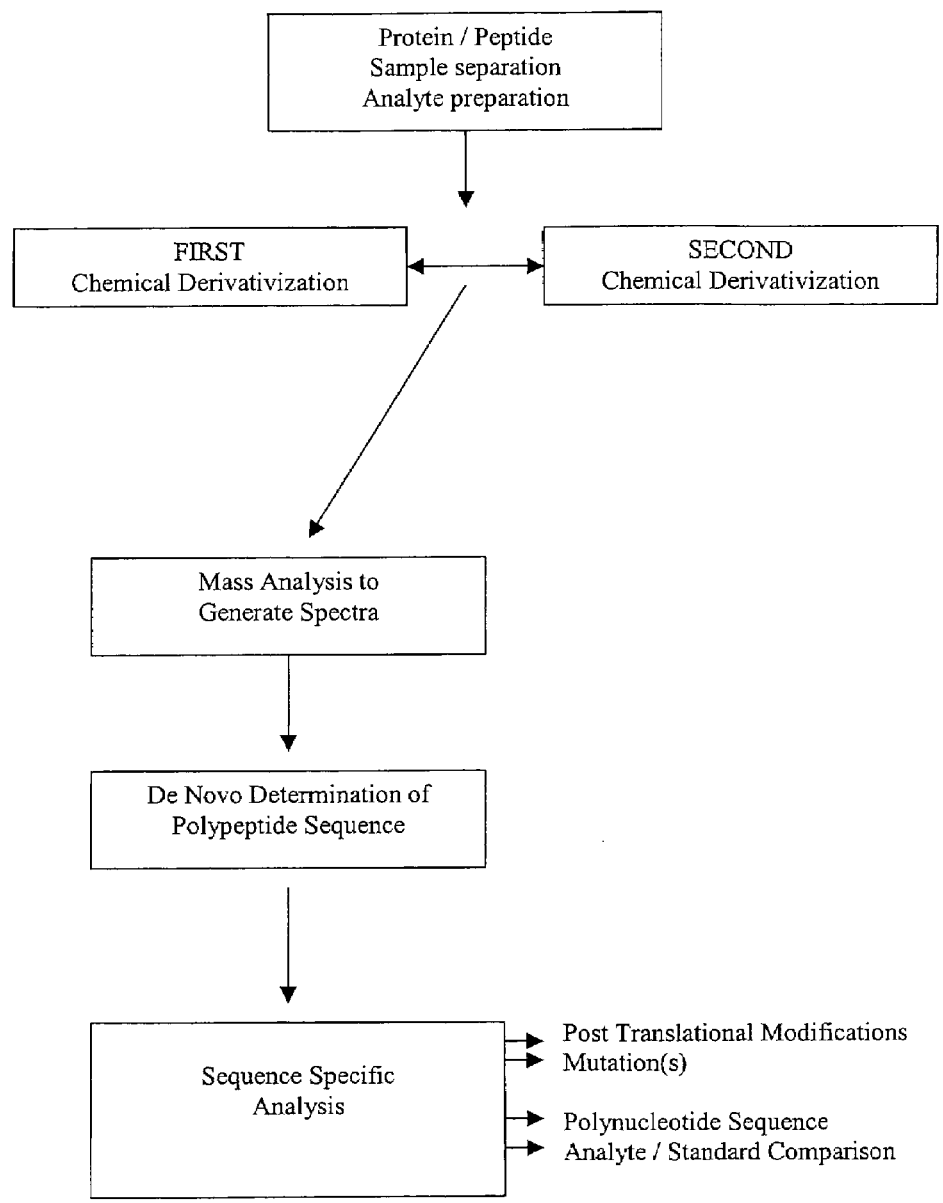
FIG. 5 is an embodiment of the method of the invention includes several optional steps in addition to the essential serial derivatization. The components of the method include analysis of the improved mass spectral data to perform a de novo peptide sequences analysis, to use sequence data in subsequent analysis and to perform any of a number of peptide analysis steps that require accurate sequence information.

Referring to FIG. 4 the MS/MS spectra resulting from a peptide (SEQ ID No: 3) having an internal arginine. Lys C is often used to digest polypeptides to increase the occurrence of C-terminal lysine residues, which increases the ability to use the experimentally-determined sequence for protein identification. However, the internal arginine residue makes the spectrum difficult to interpret, even after imidazole derivatization as shown in FIG. 4A. FIG. 4B shows the improved MS/MS spectrum from an alkylation at the carboxy groups of the acidic residues of the same peptide, showing the series of amino acid residues leading up to the internal arginine, thereby permitting the determination of a long sequence tag call.

The present invention includes kits containing reagents and instructions for performing the serial derivatizations described above. The reagents include, but are not limited to, alkylating agents, specifically methylating agents such as methanolic hydrogen chloride, activated imidazole compounds such as 2-methoxy-4,5 dihydro 1H-imidazole, buffers, solvents, and containers for each. The kits may also include reaction vessels, mixing vessels, and indicators to reveal the extent of completion of a chemical reaction. The kits include written instructions to perform the serial derivatizations described above, and may include instructions for analyzing mass data or mass spectra obtained practicing the present invention. The kits also include solid phase devices for the chromatographic clean-up of reaction products prior to mass spectral analysis.

In practice, the polypeptide analytes are analyzed using standard MS/MS equipment and systems which typically include an ionization chamber, an interface to a mass detector, a mass detector, and a data analysis system. The data analysis systems include a computer or data processor for analyzing and reporting the mass analysis data, a display unit such as a video monitor and/or a printer to display mass spectra. For sequence analysis, the computer/data processor includes software for performing sequence computations and displaying or printing amino acid sequences. The same or a separate computer/data processor may be used to submit sequence data for database analysis, protein identification, or the proteomic or genomic analyses described above.

All publication and patent application cited in this specification are herein incorporated by reference to the extent not inconsistent with the present disclosure as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention having been thus described, what is claimed as new and desired to secure as Letters Patent is:

1. A method to perform a mass analysis of a polypeptide comprising:
   (a) derivatizing the polypeptide by reacting the polypeptide with an imidazole to yield a derivatized polypeptide having an imidazole derivative of lysine;
   (b) derivatizing the polypeptide by reacting the polypeptide with an alkylating agent to yield a derivatized polypeptide fragment having an alkyl derivative of the carboxyl group of an acidic side chain of glutamic acid or aspartic acid, wherein the above derivatizing steps yield a serially derivatized polypeptide having both an imidazole derivative of the lysine and the alkylated carboxyl group; and
   (c) obtaining a mass analysis of the serially derivatized polypeptide.

2. The method of claim 1 further comprising the step of digesting the polypeptide prior to reacting the polypeptide with the imidazole.

3. The method of claim 1 further comprising determining an amino acid sequence of the serially derivatized polypeptide from the mass analysis.

4. The method of claim 1 wherein the step of reacting the polypeptide with the imidazole is performed with 2-methoxy-4,5 dihydro 1H-imidazole.

5. The method of claim 1 wherein the step of reacting the polypeptide with the alkylating agent is comprised of methylating the carboxyl group.

6. A method to determine a sequence of a polypeptide analyte comprising: (a) reacting the polypeptide analyte with an imidazole to yield a derivatized polypeptide analyte having an imidazole-derivatized lysine; (b) reacting the polypeptide analyte with an alkylating agent to yield a derivatized polypeptide analyte having an alkylated carboxyl group at an acidic side chain of glutamic acid or aspartic acid, wherein the reacting steps yield a serially derivatized polypeptide;
   performing a mass analysis of the serially derivatized polypeptide analyte; and (c) determining an amino acid sequence of the serially derivatized polypeptide analyte from the mass analysis.

7. The method of claim 6 further comprising comparing the amino acid sequence with a reference sequence.

8. The method of claim 7 further comprising determining the difference in a mass of the amino acid sequence and a mass of the reference sequence.

9. The method of claim 7 further comprising correlating the comparison to a post translational modification of the amino acid sequence.

10. The method of claim 7 further comprising digesting the polypeptide analyte prior to reacting the polypeptide analyte with the imidazole.

11. The method of claim 6 wherein the step of reacting the polypeptide analyte with alkylating agents yields a polypeptide having a methylated carboxyl group.

* * * * *

SEQUENCE LISTING

<160> NUMBER OF SEQ ID NOS: 3

<210> SEQ ID NO 1
<211> LENGTH: 8
<212> TYPE: PRT

```
<213> ORGANISM: bovine
<220> FEATURE:
<221> NAME/KEY: MISC_FEATURE
<223> OTHER INFORMATION: peptide from beta crystallin (bovine eye lens)

<400> SEQUENCE: 1

Gly Leu Gln Tyr Leu Leu Glu Lys
1               5

<210> SEQ ID NO 2
<211> LENGTH: 11
<212> TYPE: PRT
<213> ORGANISM: rabbit
<220> FEATURE:
<221> NAME/KEY: MISC_FEATURE
<223> OTHER INFORMATION: peptide from pyruvate kinase (rabbit muscle)

<400> SEQUENCE: 2

Cys Asp Glu Asn Ile Leu Trp Leu Asp Tyr Lys
1               5                   10

<210> SEQ ID NO 3
<211> LENGTH: 11
<212> TYPE: PRT
<213> ORGANISM: bovine
<220> FEATURE:
<221> NAME/KEY: MISC_FEATURE
<223> OTHER INFORMATION: peptide from cytochrome C (bovine heart)

<400> SEQUENCE: 3

Gly Glu Arg Glu Asp Leu Ile Ala Tyr Leu Lys
1               5                   10
```